(12) United States Patent
Guaragno et al.

(10) Patent No.: US 12,729,141 B2
(45) Date of Patent: Sep. 8, 2026

(54) ULTRASONIC SCALER HAVING AN OZONATED WATER SYSTEM

(71) Applicant: DENTSPLY SIRONA Inc., York, PA (US)

(72) Inventors: Kenneth R. Guaragno, Spring Grove, PA (US); Miles Hember, Cambridge (GB); Roger Millington, Cambridgeshire (GB); Carl Hewett, Cambridgeshire (GB); Samuel Whittome, Cambridge (GB)

(73) Assignee: Dentsply Sirona Inc., York, PA (US)

( * ) Notice: Subject to any disclaimer, the term of this patent is extended or adjusted under 35 U.S.C. 154(b) by 1042 days.

(21) Appl. No.: 17/766,934

(22) PCT Filed: Nov. 5, 2020

(86) PCT No.: PCT/US2020/059041
§ 371 (c)(1),
(2) Date: Apr. 6, 2022

(87) PCT Pub. No.: WO2021/092127
PCT Pub. Date: May 14, 2021

(65) Prior Publication Data

US 2024/0076210 A1 Mar. 7, 2024

Related U.S. Application Data

(60) Provisional application No. 62/930,793, filed on Nov. 5, 2019.

(51) Int. Cl.
*C02F 1/467* (2023.01)
*A61C 1/00* (2006.01)
(Continued)

(52) U.S. Cl.
CPC .......... *C02F 1/4672* (2013.01); *A61C 1/0076* (2013.01); *A61L 2/035* (2013.01);
(Continued)

(58) Field of Classification Search
CPC .......... C02F 1/4672; C25B 1/13; A61L 2/183; A61L 2/035; A61C 1/0076
See application file for complete search history.

(56) References Cited

U.S. PATENT DOCUMENTS

2002/0070123 A1* 6/2002 Andrews ................ C01B 13/10 205/626
2006/0273470 A1* 12/2006 Takahashi ................ F24F 3/14 204/228.1

(Continued)

FOREIGN PATENT DOCUMENTS

| | | |
|---|---|---|
| CA | 3159324 | 5/2021 |
| CN | 201019857 | 2/2008 |

(Continued)

OTHER PUBLICATIONS

"Canadian Application Serial No. 3,159,324, Examiners Rule 86(2) Report mailed Feb. 6, 2026", 4 pgs.

(Continued)

*Primary Examiner* — Nicholas A Smith
(74) *Attorney, Agent, or Firm* — SCHWEGMAN LUNDBERG & WOESSNER, P.A.

(57) ABSTRACT

A handpiece (108) of an ultrasonic scaler equipped with a closed system water delivery and an integrated in-line divided electrolytic cell (106) for generating ozone, one or more gas separators (116*a*, 116*b*), in-line dissolved gas monitoring and closed loop control over ozone concentration using one or more ultraviolet sensors (110).

18 Claims, 18 Drawing Sheets

(51) Int. Cl.

| | |
|---|---|
| ***A61L 2/035*** | (2026.01) |
| ***A61L 2/183*** | (2026.01) |
| ***C02F 1/461*** | (2023.01) |
| ***C02F 1/50*** | (2023.01) |
| ***C02F 1/78*** | (2023.01) |
| ***C25B 1/13*** | (2006.01) |

(52) U.S. Cl.

CPC .......... *A61L 2/183* (2013.01); *C02F 1/46104* (2013.01); *C02F 1/50* (2013.01); *C02F 1/78* (2013.01); *C25B 1/13* (2013.01); *C02F 2001/46147* (2013.01); *C02F 2001/46185* (2013.01); *C02F 2201/46115* (2013.01); *C02F 2201/4613* (2013.01); *C02F 2201/4618* (2013.01); *C02F 2201/782* (2013.01); *C02F 2209/005* (2013.01); *C02F 2209/23* (2013.01); *C02F 2209/42* (2013.01); *C02F 2303/04* (2013.01)

(56) References Cited

U.S. PATENT DOCUMENTS

| | | | | |
|---|---|---|---|---|
| 2017/0291836 | A1 * | 10/2017 | Kuzara | C02F 1/78 |
| 2018/0369619 | A1 * | 12/2018 | David | C01B 13/0207 |

FOREIGN PATENT DOCUMENTS

| | | | | | |
|---|---|---|---|---|---|
| CN | 201019857 | Y | * | 2/2008 | |
| CN | 114615953 | | | 6/2022 | |
| EP | 4054657 | | | 9/2022 | |
| JP | H1053702 | | | 2/1998 | |
| JP | H1112774 | | | 1/1999 | |
| JP | H1112774 | A | * | 1/1999 | |
| JP | 2001056292 | | | 2/2001 | |
| JP | 2001056292 | A | * | 2/2001 | |
| JP | 2001213451 | A | * | 8/2001 | B65D 75/566 |
| JP | 2007010201 | | | 1/2007 | |
| JP | 2008061700 | | | 3/2008 | |
| JP | 7638983 | | | 2/2025 | |
| KR | 20090104452 | | * | 10/2009 | |
| WO | 0033757 | | | 6/2000 | |
| WO | WO-2018100354 | A1 | * | 6/2018 | C02F 1/78 |
| WO | WO-2019147234 | A1 | * | 8/2019 | G01N 21/0303 |

OTHER PUBLICATIONS

"Japanese Application Serial No. 2022-525920, Notification of Reasons for Refusal mailed Jan. 28, 2025", (W/ English Translation), 14 pgs.

"Japanese Application Serial No. 2022-525920, Voluntary Amendment filed Oct. 16, 2024", (W/ English Translation), 17 pgs.

"Chinese Application Serial No. 202080076792.4, Office Action mailed Oct. 25, 2023", w English translation, 16 pgs.

"European Application Serial No. 20819929.9, Response filed Dec. 28, 2022 to Communication pursuant to Rules 1611 and 162 EPC filed Jun. 15, 2022", 137 pgs.

* cited by examiner

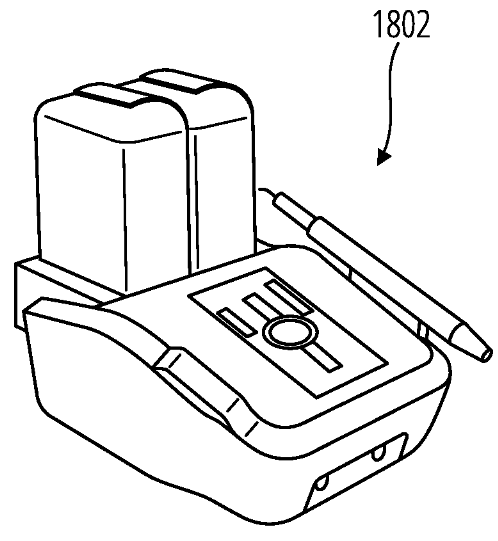
FIG. 18A
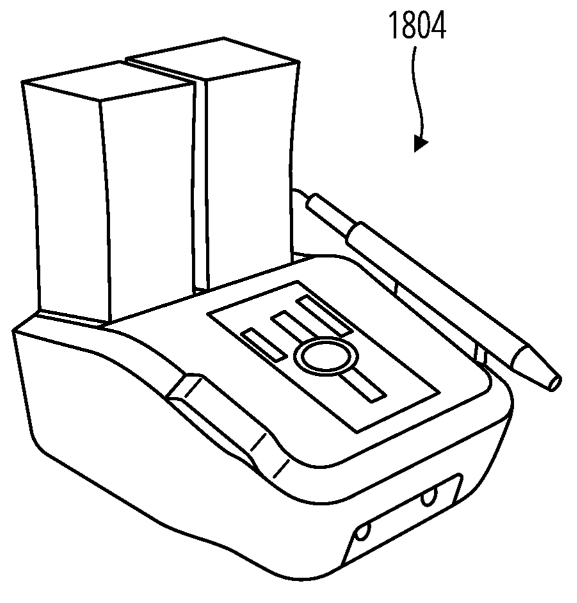
FIG. 18B
1806
1808
FIG. 18C

FIG. 22

ULTRASONIC SCALER HAVING AN OZONATED WATER SYSTEM

CROSS-REFERENCE TO RELATED APPLICATIONS

This is a National Phase application of International Application No. PCT/US20/59041, filed Nov. 5, 2020, which claims the benefit of and priority to U.S. Provisional Application Ser. No. 62/930,793, filed on Nov. 5, 2019, which are herein incorporated by reference for all purposes.

FIELD

The present application relates generally to a method, apparatus, computer system and computer readable storage media for aqueous ozone delivery and, more particularly, to a method, apparatus, computer system and computer readable storage media for providing an ultrasonic scaler with a closed system aqueous ozone delivery.

BACKGROUND

Ozone is a highly reactive gas composed of three oxygen atoms (O2). It acts as a filter for ultraviolet rays. Ozone is a highly effective antimicrobial agent and has been used in medical applications including disinfection and sterilization products. Gaseous ozone produces an oxidative reaction on the cytoplasmic membrane and cell wall of the bacteria. The resulting damage to the cell wall of the bacteria allows increased accumulation of ozone within the cell which creates free radicals that destroy the bacteria.

Ozone decays with a typical half-life of twenty minutes effecting the concentration of the aqueous ozone during transport, filling, and usage. As the efficacy of the ozone drops with time the clinician must time the ozonation and use for each scaling procedure.

Ozone can be produced by electrolyzers. In conventional electrolyzers, a goal is to produce pure hydrogen and high pressures, so a very robust structure is required. This design goal means that they are not suitable for low cost and portable devices. Moreover, it is common for conventional electrolyzers to have very low levels of dissolved ozone in the solution, due to the requirement to avoid releasing excessive gaseous ozone. Currently, no commercial small scale electrolyzer is able to produce a controlled level of dissolved ozone at higher levels. Moreover, time management is well known to be the most stressful part of a dental clinician's day. Waiting on equipment to startup and come up to charge would be unacceptable. Conventional ozonation processes that use corona discharge to produce ozone gas from compressed oxygen or room air must bubble the ozone into the water. This can be achieved by a sparger or venturi that injects gas directly into the water line, alternative system architectures that perform this gas dissolution under pressure may approach the charging rates of the electrolytic ozone generation architecture described in this disclosure, however they are limited in their ability to produce and dissolve ozone with the control and flux while at the same time maintaining a small form factor. Methods used today for producing a batch of aqueous ozone are performed at or near 1 atm, requiring as much as 20 to 30 minutes to fully charge a liter of water with ozone to achieve a clinically useful concentration (e.g. 4 ppm).

Further, the key to successful periodontal therapy and maintenance is elimination or reduction of pathogenic bacteria from periodontal pockets and establishment of microbiota compatible with periodontal health. Current methods used for periodontal debridement include both power scalers and manual instrumentation. Modern techniques used for debridement rely primarily on the disruption of both hard and soft deposits. Soft deposits are primary formed by microorganisms that attach to surfaces and develop complex structures made up of microbial cells and biopolymers (i.e. EPS, extracellular polymeric substances). Dysbiosis occurs when a healthy homeostasis shifts, and an imbalance of pathogenic bacteria becomes established. The goal of periodontal debridement is to restore gingival health by completely removing elements that provoke gingival inflammation (i.e. plaque, calculus, endotoxin). Proper periodontal therapy disrupts and removes, subgingival biofilm, endotoxins, plaque-retentive factors such as calculus. Modern periodontal therapy has the added goals of improving patient comfort, conservation of tooth structure, creation of a biologically acceptable root surface, and the resolution of inflammation.

An ultrasonic scaler combines acoustic energy which excites the fluid around the scaler tip creating microstreaming, and cavitation, while also delivering both mechanical debridement and the constant flushing from the lavage directed at the surface being debrided. Scaling procedures rely on the lavage to maintain safe operating temperatures for the scaler handpiece and tip, flush away deposits and debris, and provide the medium for coupling the ultrasonic acoustic energy onto the surrounding surfaces being cleaned.

Most ultrasonic scaling procedures utilize potable water or water treated to maintain the cleanliness of the scaling equipment and other waterlines. In addition, medicament may be used for periodontal debridement, suitable medicaments include Chlorohexidine, Provodine Iodine, Hydrogen Peroxide along with other mouth rinses and antimicrobials. These medicaments each have limited potential and toxicity depending on their concentration.

BRIEF SUMMARY

The illustrative embodiments provide a device, method, system and a computer readable media. In an aspect herein, an ultrasonic scaling device having the ability to generate aqueous ozone on demand is provided. It may utilize aqueous ozone lavage to enhance the removal of dental biofilm for debridement. Aqueous ozone is delivered to the oral cavity through the ultrasonic scaler handpiece and insert, which are controlled by a system described herein. The goal is to deliver effective and safe levels of aqueous ozone to improve clinical outcomes (e.g., bleeding on probing, clinical attachment loss, inflammation of the periodontium).

The illustrative embodiments recognize that ozone is effective in reducing the bacterial burden in the oral microbiome. This has significant benefits for oral health and wider systemic health, including reducing risk of caries, gingivitis and periodontitis, halitosis, cardiovascular disease, stroke, hyperglycemia, and other diseases.

The illustrative embodiments also recognize that an ultrasonic scaler with the ability to produce and control the delivery of aqueous ozone addresses key market barriers. Practices need not buy a separate ozone generator in addition to an ultrasonic scaling unit. Practices would not need to ozonate water, transport, and fill an ultrasonic scaler reservoir.

In an aspect herein, a method of providing ozonated water to an ultrasonic scaler handpiece comprising is disclosed. The method includes: delivering water from a water supply to an electrolytic cell of an aqueous ozone ultrasonic scaler system; delivering current to the electrolytic cell to generate ozone gas in the water; providing one or more recirculation loops in a fluid pathway to move the water and ozone gas through the electrolytic cell and one or more gas separators that correspond to the one or more recirculation loops; controlling a level of ozone gas concentration in the water through an amount of the current delivered to the electrolytic cell in order to generated ozonate water having a defined concentration of dissolved ozone; and separating gaseous ozone from a flow of the ozonated water that is to be delivered to a handpiece using the one or more gas separators.

In another aspect disclosed herein, the method includes any combination of the following: (i) further comprising providing one or more pumps to maintain a defined fluid level and pressure of the aqueous ozone ultrasonic scaler system in order to increase solubility of the ozone gas in the water, (ii) further comprising: switching, responsive to providing two or more recirculation loops, an electrical polarity of the electrolytic cell after a defined period of operation time and after verifying that ozone gas in the water has decayed, such that a side of the aqueous ozone ultrasonic scaler system that was a cathode side in a previous operation becomes the anode side in a current operation and another side of the aqueous ozone ultrasonic scaler system that was the anode side in the previous operation becomes the cathode side in the current operation, in order to distribute a membrane degradation, that occurs from an interaction of ozone gas and other oxidative species from the electrolytic cell, over both sides of the electrolytic cell in order to extend a shelf life of a membrane of the electrolytic cell, (one or more membranes may be used. Each membrane is mechanically interlocked with the electrode, therefor using two membranes decouples the electrodes to prevent the membranes from seeing high mechanical shear stress. In an illustrative embodiment, three or four or more membranes can be stacked) (iii) wherein the switching eliminates or substantially eliminates stagnant water and microbial contamination, (iv) wherein the water delivered from the water supply is deionized water or water obtained from reverse osmosis (low conductivity water concentrates the current density at the triple phase boundary improving ozone generation and prevent fouling from mineral deposits on the electrodes), (v) further comprising: slowing a flow of the ozonated water entering the one or more gas separators using an inlet baffle such that in order to substantially reduce overturning flow in a chamber of the one or more gas separators and prevent bubbles from being carried to an exit port of the one or more gas separators. This also prevents bubbles from entering the recirculation loop eliminating bubble interference with the optical ultraviolet light absorbance ozone sensor.

In another aspect herein an apparatus for providing ozonated water to an ultrasonic scaler handpiece is disclosed. The apparatus comprises: a water supply for delivering water to an electrolytic cell of an aqueous ozone ultrasonic scaler, the electrolytic cell in connection with the water supply through a fluid pathway and is adapted to receive current to generate ozone gas in the water in order to form ozonated water; one or more gas separators, each gas separator is disposed in a corresponding recirculation loop of the fluid pathway that also contains the electrolytic cell, said each gas separator is configured to separate gaseous ozone from a flow of ozonated water that is to be delivered to a handpiece; and one or more ultraviolet sensors disposed in said recirculation loop of the fluid pathway, the one or more ultraviolet sensors are adapted to measure dissolved ozone concentration in the water through an amount of ultraviolet light absorbed by a portion of the water passing through the water.

In yet another aspect one or more combinations of the following features of the apparatus are disclosed: (i) further comprising: one or more pumps disposed in the fluid pathway to control a pressure of apparatus in at least a portion of the fluid pathway, (ii) further comprising: one or more valves disposed in the fluid pathway to release gas in order to control another pressure of apparatus in at least a portion of the fluid pathway, (iii) further comprising: one or more level sensors connected to the one or more gas separators to measure a level of ozonated water in the gas separators, (iv) further comprising: an ozone destroyer disposed in a gas release pathway of one or more gas separators and adapted to convert separated gaseous ozone gas into oxygen, (v) wherein the water supply is a spout pouch or water bottle having a duck bill connection assembly to deliver the water in a single direction, (vi) wherein the water supply is held in a loading tray in a base of the apparatus, (vii) wherein a polarity of the electrolytic ozone cell is switchable to reverse a side of the apparatus that produces the ozone gas.

In a further aspect, a computer system for providing ozonated water to an ultrasonic scaler handpiece is disclosed. The computer system comprising a processor configured to perform the steps of: delivering water from a water supply to an electrolytic cell of an aqueous ozone ultrasonic scaler system; delivering current to the electrolytic cell to generate ozone gas in the water; providing one or more recirculation loops in a fluid pathway to move the water and ozone gas through the electrolytic cell and one or more gas separators that correspond to the one or more recirculation loops; controlling a level of ozone gas concentration in the water through an amount of the current delivered to the electrolytic cell in order to generate ozonate water having a defined concentration of dissolved ozone; and separating gaseous ozone from a flow of the ozonated water that is to be delivered to a handpiece using the one or more gas separators.

In an even further aspect, a non-transitory computer-readable storage medium storing a program which, when executed by a computer system, causes the computer system to perform a procedure is disclosed, the procedure comprising: delivering water from a water supply to an electrolytic cell of an aqueous ozone ultrasonic scaler system; delivering current to the electrolytic cell to generate ozone gas in the water; providing one or more recirculation loops in a fluid pathway to move the water and ozone gas through the electrolytic cell and one or more gas separators that correspond to the one or more recirculation loops; controlling a level of ozone gas concentration in the water through an amount of the current delivered to the electrolytic cell in order to generate ozonate water having a defined concentration of dissolved ozone and measured via the ozone absorbance property of ultraviolet light; and separating gaseous ozone from a flow of the ozonated water that is to be delivered to a handpiece using the one or more gas separators.

A fully integrated system with inline aqueous ozone generation enables aqueous ozone to be generated and used in the operatory when needed for a procedure. The materials used in the fluid pathway/fluidic path for both the aqueous ozone generator and the scaler are controlled and engineered to limit scavenging and ensure material compatibility with the dissolved ozone, control the concentration of the lavage that exits the scaling instrument and ensure efficacy and reliability of the equipment. Developing and integrating the ozone generator and ultrasonic scaler prevent the misuse of aqueous ozone in existing scalers that are incompatible with ozone.

In an aspect herein, dental professionals are able to use the ultrasonic scaling unit with or without generating aqueous ozone. Having the ability to turn off the ozone or lower it so that it only maintains the cleanliness of the waterlines provides the clinician with the ability manage when they deliver aqueous ozone to their patients.

To create aqueous ozone and achieve associated clinical benefits specially formulated water different from municipal water may be needed. Varying levels of flora and other forms of water different from said specially formulated water may contain chemicals and/or additives. The specially-formulated water can come in, for example, 4 liter bottles corresponding to 2-4 patients. The water is delivered in a container with a proprietary fitment that is designed to mate with a scaler water interface and prevent refilling. By controlling the input water, the system reliability and lavage quality and efficacy can be controlled.

In an illustrative embodiment, the system significantly improves periodontal clinical parameters (e.g., bleeding on probing (BOP), clinical attachment loss, etc.) as compared to conventional methods of debridement by combining the efficacy of ultrasonic scaling with the antimicrobial and antibiofilm attributes of aqueous ozone. Recolonization of a cleaned pocket with a more benign flora is more likely when the pathogenic population has been more completely removed. A goal of sustained periodontal treatment is to achieve a durable microbial shift in these regions from a pathogenic (dysbiotic) flora to a more benign population that is less harmful to the local tissue and which can remain in reasonable equilibrium with the host tissue and physiology. The result is a reduction in inflammation of the periodontium facilitating improved clinical parameters for patients being treated for gingivitis and periodontal disease better than any other method of debridement. The Aqueous ozone combined with ultrasonic scaler modes of action (i.e. mechanical, cavitation, micro-streaming, and flushing action of the lavage) eradicates pathogenic bacteria, slowing the formation of the dysbiotic pathogenic subgingival biofilm and plaque better than any other method of debridement. Consequences may include significant improvements in oral freshness, reduced gum inflammation, and long-term retention of teeth. By scaling with aqueous ozone, the ozone reduces infectious aerosols derived from patient bacteria present in the oral cavity during ultrasonic scaling. Since the system will not be exposed to tap water and all the fluid in the system will be ozonated suppressing the formation of biofilms in the system tubing and water path and enabling water lines of the ultrasonic scaling system to remain near bacteria free, i.e. less than 100 colony forming units (CFUs) and possibly as low as 5 CFUs when performing clinical procedures (e.g., scaling, SRP). Although antimicrobial agents (e.g. Chlorohexidine, hydrogen peroxide, Sodium Hypochlorite, Provodine Iodine) exist today and systems are available for delivering them into an ultrasonic scaler lavage the ozone and oxygen-infused water generated by this system which eradicates pathogenic bacteria is natural and free from additives or chemicals. Aqueous ozone decomposes so rapidly, into water and oxygen, it will not remain active in the periodontal pocket and has lower cytotoxicity than other antimicrobials. It has no impact on taste and does not cause staining. By combining an ultrasonic scaler primary mode of action (e.g. mechanical, acoustic microstreaming, cavitation, and flushing lavage) with aqueous ozone both hard and soft deposits can be debrided without the addition of any extra steps or adjunctive therapy. The combined technology eradicates pathogenic bacteria and disrupts biofilm sub-gingivally without the need for additional treatments (e.g., adjunctive medication, hand instrumentation, subgingival air polishing, etc.).

Thus, the illustrative embodiments recognize that Aqueous ozone (AO) is an advantaged option for delivering the antimicrobial functions in the lavage, replacing the need for conventional antimicrobial additives. Ozone in solution is a broad-spectrum antimicrobial, able to deactivate bacteria, fungi, and viruses, and against which resistance cannot develop. Furthermore, aqueous ozone accelerates the removal of biofilm, shortening the scaling procedure or increasing the completeness of biofilm removal. The chemical action of aqueous ozone on biofilm extends the effective radius of action of the scaling, and also attacks biofilm that is physically inaccessible. Aqueous ozone is highly effective at degrading biofilm and killing microbial cells, but has low toxicity to the patient's tissues as is described in the publication by Karin C. Huth et al., entitled "Effect of ozone on oral cells compared with established antimicrobials" Eur J Oral Sci. 2006: Vol. 114: pp 435-440, which is incorporated by reference herein in its entirety, as if set forth fully herein.

The use of aqueous ozone lavage can allow reduced ultrasonic power with the same cleaning efficacy, which reduces discomfort to the patient. Optimizing the results from an aqueous-ozone scaling method requires joint control of parameters and hence an integrated scaler with ozone generating and delivery means is highly preferable. The system provides all the essential means to deliver an optimized safe and effective ozone-enhanced scaling treatment.

BRIEF DESCRIPTION OF THE SEVERAL VIEWS OF THE DRAWINGS

To easily identify the discussion of any particular element or act, the most significant digit or digits in a reference number refer to the figure number in which that element is first introduced. Certain novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

FIG. 18A depicts an alternate configuration of a system in accordance with one embodiment.

FIG. 18B depicts an alternate configuration of a system in accordance with one embodiment.

FIG. 18C depicts an alternate configuration of a system in accordance with one embodiment.

20B depicts an alternate configuration of a system in accordance with one embodiment.

Figure 20A:
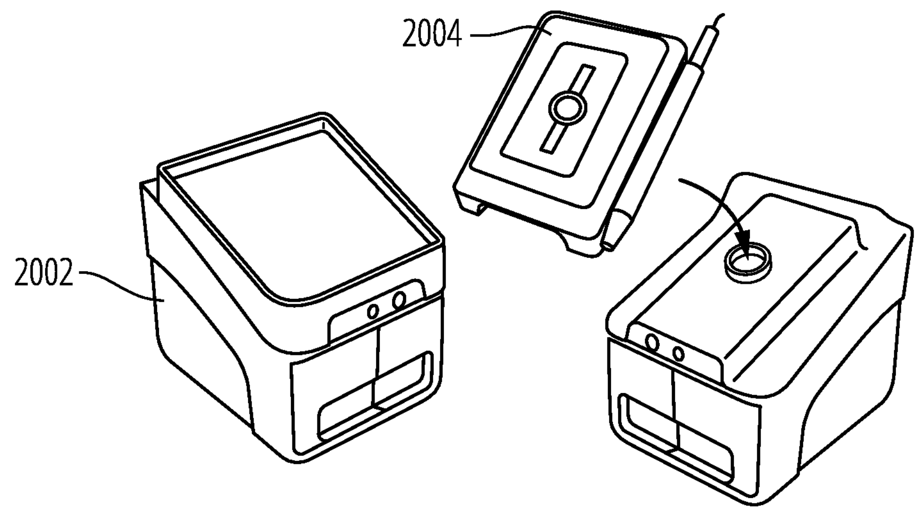

FIG. 20A depicts an alternate configuration of a system in accordance with one embodiment.

Figure 20B:
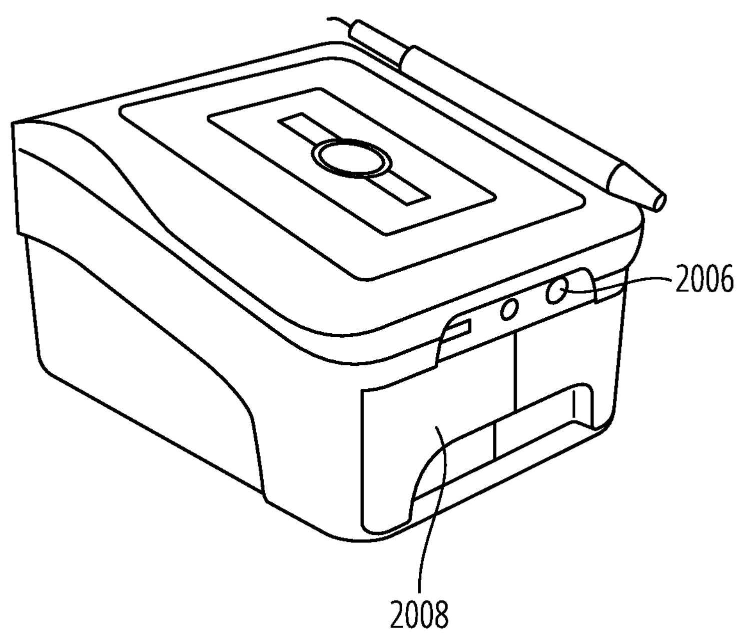
Figure 21:
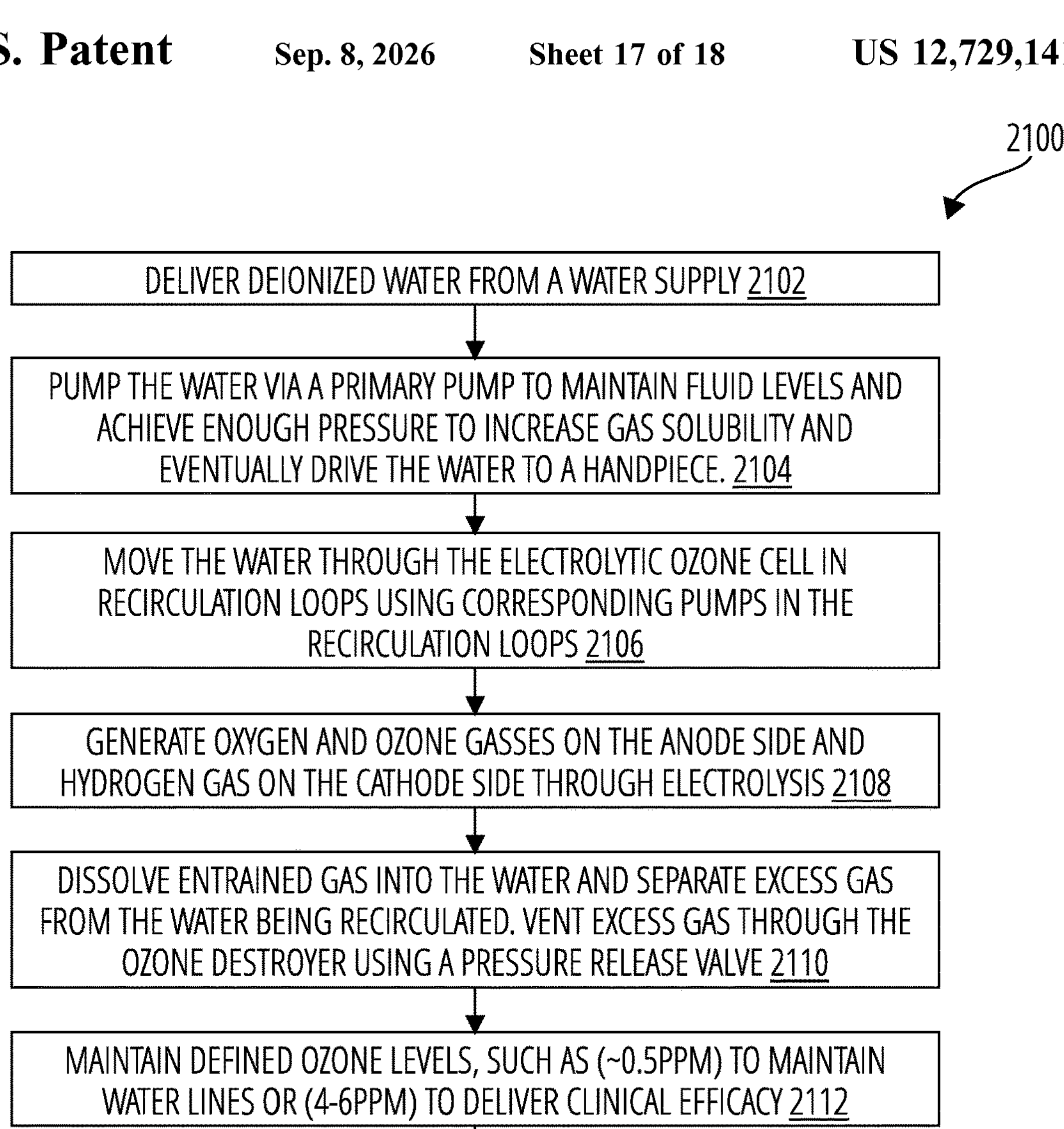

FIG. 20B depicts an alternate configuration of a system in accordance with one embodiment FIG. 21 is a flowchart showing a method in accordance with one embodiment.

Figure 22:
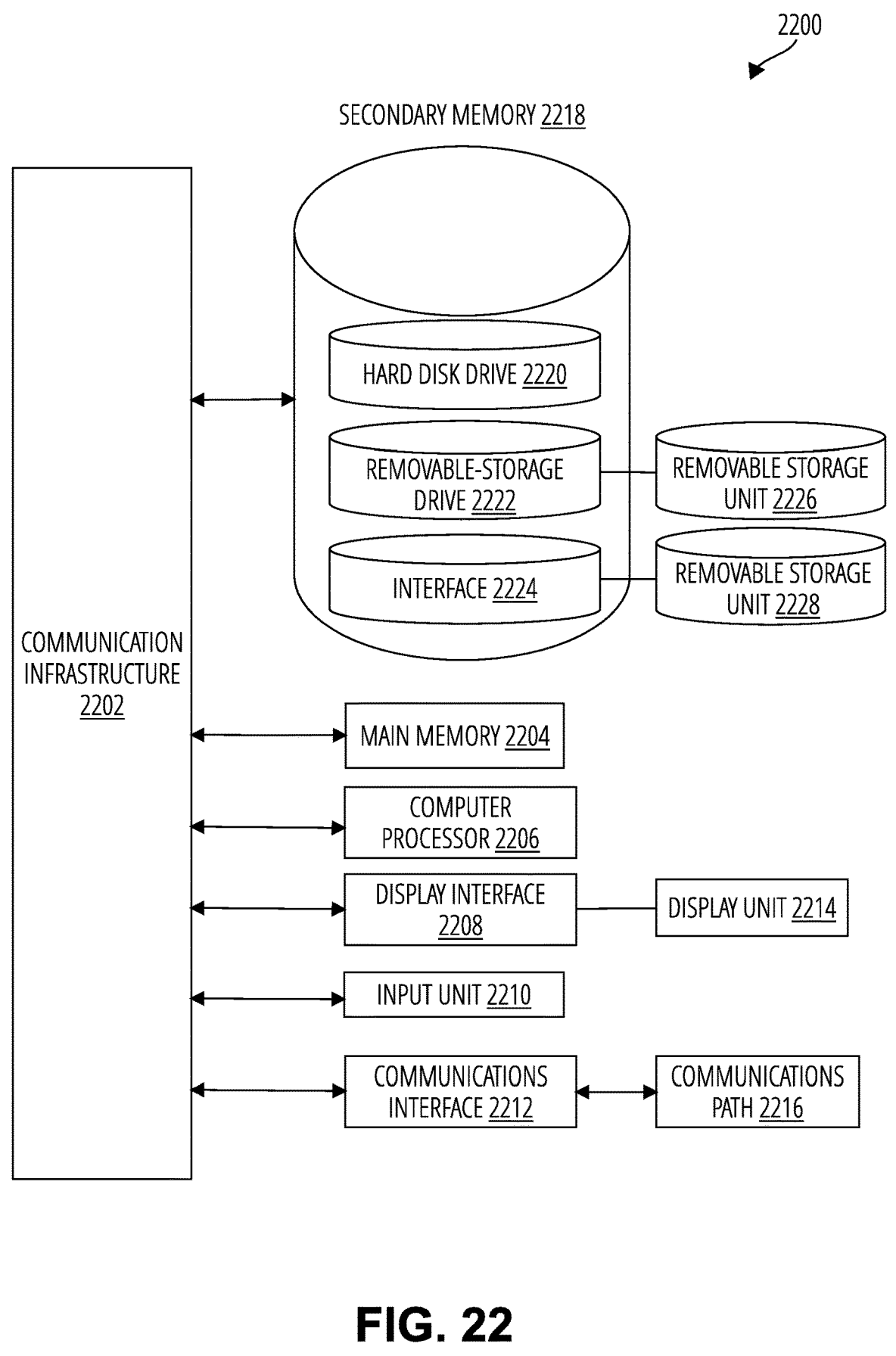

FIG. 22 illustrates a computer system in accordance with one embodiment.

DETAILED DESCRIPTION

The illustrative embodiments described herein are directed to an ultrasonic scaler having aqueous ozone. The ultrasonic scaler comprises a water source, electrolytic cell, gas separator, ozone destroyer, pumps and handpiece, which are described hereinafter.

System and Apparatus

Figure 1:
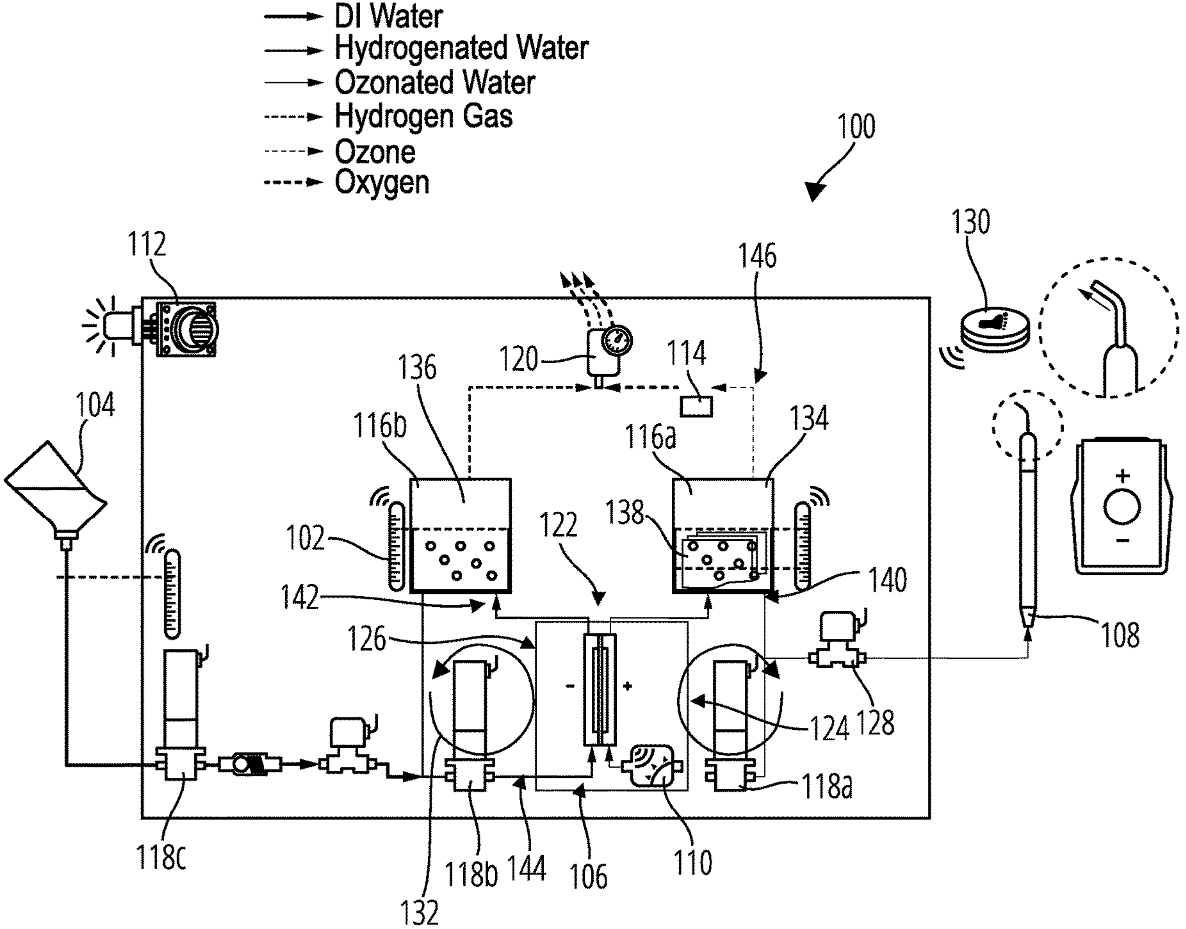
FIG. 1 depicts a block diagram of a system in accordance with one embodiment.

FIG. 1 depicts a block diagram of an aqueous ozone ultrasonic scaler system 100 in accordance with one embodiment. The system includes a water supply 104 adapted to enable safe, long term operation of the system. In an illustrative embodiment, the water supply is purified water such as deionized water or water obtained from reverse osmosis, in particular with negligible levels of multivalent metal ions. Optional water compositions comprising a selected concentration of dissolved carbon dioxide, or oxygen, or of an inert gas can be used in the proposed system. The water supply 104 may be delivered in a package/water bottle/spout pouch 704 such as a 200 to 1000 ml package with a fitment to protect the system from being fed with water that may foul the cell or produce unwanted constituents upon ozonation (e.g. bromine to bromide, or prochlorites). The aqueous ozone ultrasonic scaler system 100 has one, two, or more water supplies 104 attached. The system has the ability to automatically switch from one water supply 104 to another water supply 104 in the event a water supply 104 (spout pouch 704) empties during the procedure, thus preventing the clinician from being interrupted while treating a patient. The system alerts the clinician that the package is empty and needs to be replaced prior to starting a second procedure. The water supply 104 has a fitment that prevents refilling. In an illustrative embodiment, the system identifies if a package has been refilled by either looking for a connection force or reading an RFID label that prevents reuse and the use of alternative water sources.

The aqueous ozone ultrasonic scaler system 100 also includes an electrolytic ozone cell 106 that oxidizes the water to form ozone in solution. Conventional cells also produce some oxygen as a byproduct, which further increases the utility of the produced water for treatments targeting anaerobic organisms, but in any case, does not decrease the value of the aqueous ozone (AO) solution for the primary purpose of scaling. Cells may also produce some hydrogen peroxide, and this component of the solution is also beneficial for cleaning, bleaching, and antimicrobial effects. In some cases, a synergistic effect of ozone and hydrogen peroxide is known and can be advantageously used by the system.

The system is able to change the ozone levels in the system at startup more rapidly by driving the electrolytic ozone cell 106 with more current than is needed to maintain appropriate levels during runtime and idle time. During startup the system attains a defined pressure by two means, a primary water pump 118*c* that both fills and pressurizes the system with water and an air pump 118*a* (or air pump 118*b*) that assists the primary water pump 118*c* on the gas side of the system to produce sufficient system operating pressure needed to drive fluid to a scaler handpiece.

In an illustrative embodiment, a monitoring and control device enables the production of a stable and known concentration of the active species under the control of the user. Ozone is a potent oxidizer and the system should enable automatic monitoring and control of the produced concentration to assure safety and efficacy.

A gas separator 116*a*, gas separator 116*b* separates gaseous ozone from the flow of water delivered to the ultrasonic handpiece 108. Gaseous ozone is irritant and does not usefully increase the efficacy of scaling, and so the aqueous ozone ultrasonic scaler system 100 is adapted to provide all of the ozone to the instrument in solution, with minimal content of bubbles. The system also includes means to ensure that the flow paths within the system are sufficiently free of bubbles to enable operation of components such as ozone sensors or pumps. Similarly, the system includes a means to separate out gaseous hydrogen for removal from the cathode, which avoids the need to have a hydrogen peroxide waste stream from a depolarizing cathode. The system is adapted to separately optimize the flow conditions in the electrolytic ozone cell 106 from the flow demands of a clinician. For example, a buffer volume in the gas separator is used to decouple instantaneous flow in the cell from the delivered flow rate. The use of a buffer volume 134 and a recirculation loop 132 allows for an internal flow rate that is higher than the net flow from inlet to outlet, allowing for independent variation of flow rates according to requirements. In practice, this has additional advantages in providing a well-mixed system volume for accurate concentration measurement and controlled delivery to the ultrasonic handpiece 108, and it also enables the integration of a gas separator 116*a*, gas separator 116*b*, and an in-line sensor 102 that has a faster response time than one in a stagnant storage volume.

Further, the system includes a means of controlling the flow and ozone content of the water to the handpiece in response to user controls and set preferences, combined with meeting other requirements such as for cooling or coupling of ultrasound to the target surface. The disclosure contemplates a dynamically controlled water flow and ozone level that responds to usage and instrument parameters such as power level. (e.g. if the tip is not in contact with the target surface, as inferred from the ultrasonic parameters, the excitation power can be momentarily reduced, and the water flow reduced as well. When "active" scaling happens, both power and water flow can instantly be increased by the control system. The adaptive behavior can provide substantial usability advantages to the system and can reduce the need for manual controls to be operated. Moreover, the system contemplates controlling system operating pressure to operate the system at an elevated pressure to cause more dissolution of ozone in the generating loop and to provide water at a pressure sufficient to operate a standard scaling instrument, allowing use of existing equipment. Moreover, the pressure may be controlled to provide pressure signals that can be used as part of the flow control method, for example when filling the system, and for controlling the venting of gas produced by the electrolysis. In further embodiments, the system can be adjusted to operate at one of a number of different pressure settings, and the electrolytic cell operating point can be adapted to compensate for the amount of gas dissolved at the different pressures.

An ozone destroyer 114 is also used to neutralize any unwanted ozone that would otherwise be released by the system e.g. as part of the gas separation function. Also, a means of managing any associated hydrogen release from the cathode of the electrolytic cell. Hydrogen can be oxidized back to water either in the cell itself, or in a separate component optimized for that function, or in conjunction with the reduction of the excess ozone. The ultrasonic handpiece 108 is adapted to function with increased efficacy in the context of an ozone-rich lavage. Adaptations can comprise e.g. coatings that increase the compatibility of the handpiece with the ozone solution, an ultrasonic exciter with low heat output, sensing device that connects to a drive unit, a recirculating water flow option, or dual-flow design that uses plain water for cooling and basic lavage and on-demand ozonated lavage delivered directly to the tip only.

Moreover, the system includes a user interface 402, a physical interface to a water supply (not shown) and to a handpiece, and a suitable casework to adapt the system optimally to the needs of a dental practitioner and the safety and efficacy of the relevant procedures. In an initial embodiment, the system functions very similarly to a conventional non-ozonated ultrasonic scaler so that skilled users can immediately use the new system in established procedures. Integration of the control of the ultrasonic and ozone-producing functions is a valuable feature of the proposed embodiments.

The system is inherently safe and by design has several attributes that provide both safety and efficacy. The system thus delivers aqueous ozone, no ozone in the gaseous form is delivered to the patient. The flow rate of aqueous ozone is limited by the systems low pressure, flow control, and orifice in the ultrasonic scaler insert. Ozone production is inherently safe, controlled by Faraday's law of electrolysis, gas production directly proportional to electrical current. As a result, the Electrolytic ozone (EO) generated is directly limited by the DC current sent to the EO generator. The presence of water in the system is required for the electrolytic generator to produce aqueous ozone, the ozone generator 122 may be configured to not operate or produce ozone gas in the absence of water. UV sensor 110 directly monitors the level of ozone in the water. The Faradaic control establishes safe operating areas such that the cell drive parameters can provide both control and monitoring of the cell condition, as the electric current and resultant cell voltage are what drive the electrochemical reaction. The system ozonates high purity water delivered in a custom container with a proprietary connection, providing control over both the input water quality and composition found in the ozonated lavage. Unlike other systems that attempt to ozonate tap water or dissolve gas produced from room air via corona discharge. Safety of lavage is controlled by the input water, ozone compatible materials used to build system, and gas separator that prevents gas and entrained gas from be delivered to the ultrasonic scaler handpiece. Excess ozone gas is neutralized by its conversion to oxygen (O2) via an ozone destroyer, preventing the deliberate release of ozone into the local ambient through a gas release pathway 146. Protection from unwanted discharge of ozone from system (i.e. leak) is provided by robust tubing, fittings, and components (i.e. Pumps and valves). The system controls prevent ultrasonic operation if system state is not ready to deliver lavage (i.e. empty fresh water source, target ozone level not met, system pressure not achieved, or faults detected)

Having briefly described components of the aqueous ozone ultrasonic scaler system 100, said components will now be described in more detail.

In an illustrative embodiment, the water supply 104 is pre-formulated in individual packages as shown in FIGS. 17-19. The packages are made sterile, with a suitable aseptic connection (not shown) to the system. To ensure continuity of supply during a procedure, the system is adapted to allow a plurality, for example, two containers and to change-over between them if the first should empty during a treatment. In an illustrative embodiment, the system determines that the correct water package has been inserted, to ensure safe and optimal operation of the system.

Figure 15:
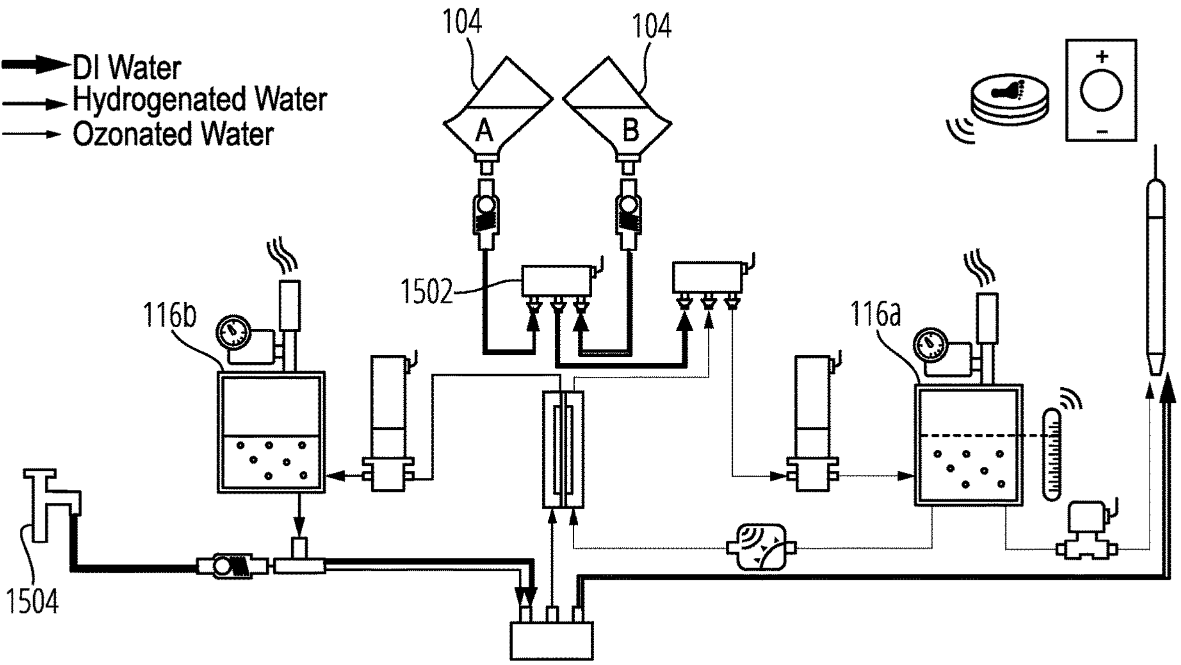
FIG. 15 depicts a system in accordance with one embodiment.

In another illustrative embodiment as shown in FIG. 15, real-time purified water from a potable water source is incorporated. Herein, a separate purifier supplying, or an integrated purifier is used to purify the tap water 1504. The purifier-fed system includes a water-quality sensor to ensure correct operation for the safe supply of the electrolytic cell. In the case where an external purifier is used, a small secondary purification stage may be included with the specific function of removing any remaining traces of ions such as Fe, Cu, Zn, or Al that are known to have high affinity for the membrane and also to promote membrane degradation processes. In particular, an integrated water-purifying mechanism can use conventional reverse osmosis/deionization technologies, or preferably, use a self-regenerating deionization technique such as electrodeionization, capable of taking a standard potable water feed/non-ozonated water and producing a sufficient flux of purified water for the average use rate of the system. An intermediate water reservoir may be used to enable buffering between the peak demand and the average demand, at the expense of making the system occupy more space. The tap water 1504 is typically available at a defined pressure, and this pressure may be used to drive the initial filtration step in the purification process, thereby reducing the need to include a separate pump in the system for this purpose only. The system is adapted to allow for operation from a plumbed-in water supply in addition to the bottle-fed configuration, to allow the operator to select non-ozonated operation at any time and to avoid depleting the pure water supply when it is not actually needed. Unless the plumbed supply is filtered and deionized, it is not preferred to use it in the electrolytic ozone generator. The plumbed in water supply would not travel through the ozone generator 122 portion of the system but instead be delivered through a bypass water line with its own control over water pressure and a separate water solenoid to enable and disable water output to the handpiece. The system may also be designed without an external connection for plumbed-in water; however, it may still be equipped with a bypass line that draws water from the bottle-fed configuration and directly, without ozonation, delivers it to the handpiece. Non-ozonated operation can also be delivered through the ozone generator 122 portion of the system by turning off the current to the electrolytic ozone cell 106, the cell current can also be operated at a significantly lower level or pulsed infrequently at a current necessary to produce ozone, so that a non-detectable level of ozone is delivered to maintain the cleanliness of the waterlines in the system.

Figure 2:
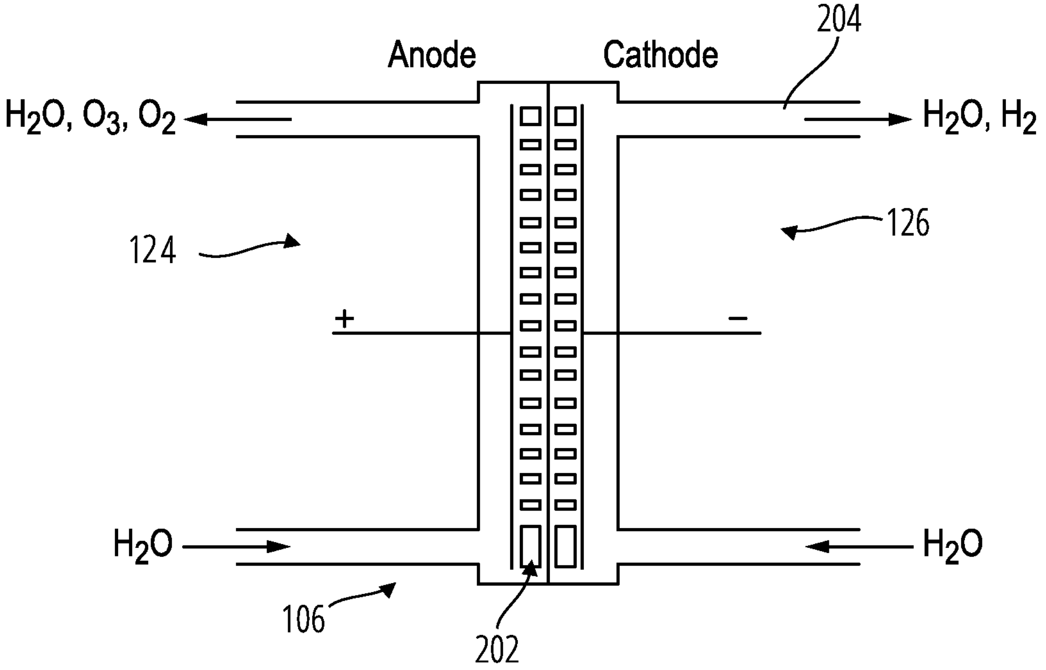
FIG. 2 depicts a sketch of an electrolytic cell in accordance with one embodiment.

FIG. 2 depicts a sketch of an electrolytic cell in accordance with one embodiment. Electrochemical ozone generation by direct oxidation of water, in place of the formation of O3 from O2 in the gas phase, is a complex electrochemical process in which the catalytic electrode surface is the site of a network of reactions via several different adsorbed intermediates. The network of reactions produces a mixture of oxygen and ozone. The chemical properties of the catalyst surface affect the proportion of ozone production, but the oxygen-forming pathway is energetically more favorable and typically at least half of the electrode current forms oxygen even on the most ozone-promoting surfaces.

A goal is to achieve as high a rate of oxygen evolution (and hence hydrogen production) as possible, at the lowest achievable cell voltage, because this directly influences the energy cost of the process. Much of the electrolysis is done directly, with a conductive electrolyte carrying the current between the electrodes, but a membrane 202 (proton-conductive membrane) can be used to carry a proton current but not allow other species to pass at appreciable rates. This allows electrolysis of pure water to be achieved, with significant advantages in terms of chemical simplicity and absence of unwanted byproducts. The membrane 202 can be sulfonated derivatives of Teflon, such as Nafion, Aquivion, and similar products. These cells are usually called Proton Exchange Membrane Water Electrolysers (PEMWE). PEMWE industrial cells in e.g. the so called "Membrel" process for oxygen/hydrogen production can have long working lifetimes. However, when the cell voltages are increased and ozone-selective catalysts are used, the achievable working lifetime decreases considerably, due to membrane and electrode degradation in the extremely oxidizing environment, and in particular due to some free radical mediated reactions that effectively attack the membrane polymer.

The selective formation of ozone instead of oxygen has hydrogen as a waste product. With a target of the aqueous ozone ultrasonic scaler system 100 being to achieve a combination of a high dissolved ozone concentration and a long working lifetime of the cell, electrodes of boron doped diamond (BDD) can be used, to take advantage of this material's preferential ratio of ozone to oxygen formation. However, BDD as a material presents some practical challenges, as it is essentially equivalent to diamond in terms of mechanical properties and has to be made by direct synthesis of a doped diamond layer on a suitable substrate to form a layer of controlled conductivity. Thus, a BDD electrode is a relatively expensive and fragile component. In an illustrative embodiment, the electrolytic ozone cell 106 comprises a pair of perforated silicon plates with a thin boron doped diamond coating, with a layer of proton conducting membrane 202 between them, and flow passages 204 for the water and released gases to pass over the perforated surfaces. This configuration provides the necessary 3-phase boundary regions at the edge of every hole in the plate. Of course, other similar arrangements can be obtained in light of this specification. The examples in this disclosure are used only for the clarity of the description and are not limiting to the illustrative embodiments. Additional operations, actions, tasks, activities, and manipulations will be conceivable from this disclosure and the same are contemplated within the scope of the illustrative embodiments.

Figure 3A:
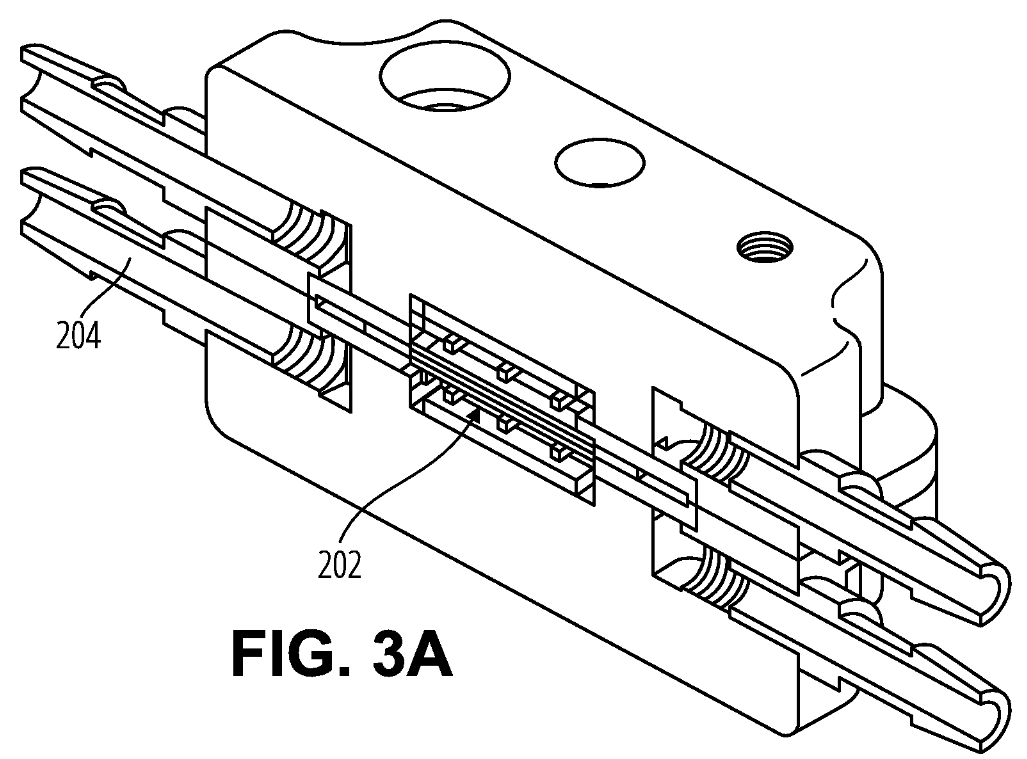
FIG. 3A depicts a perspective view of an electrolytic cell in accordance with one embodiment

FIG. 3A depicts a perspective view of a first configuration of an electrolytic ozone cell 106 in accordance with one embodiment. In this configuration, the flow passages 204 are arranged parallel to the membrane 202.

Figure 3B:
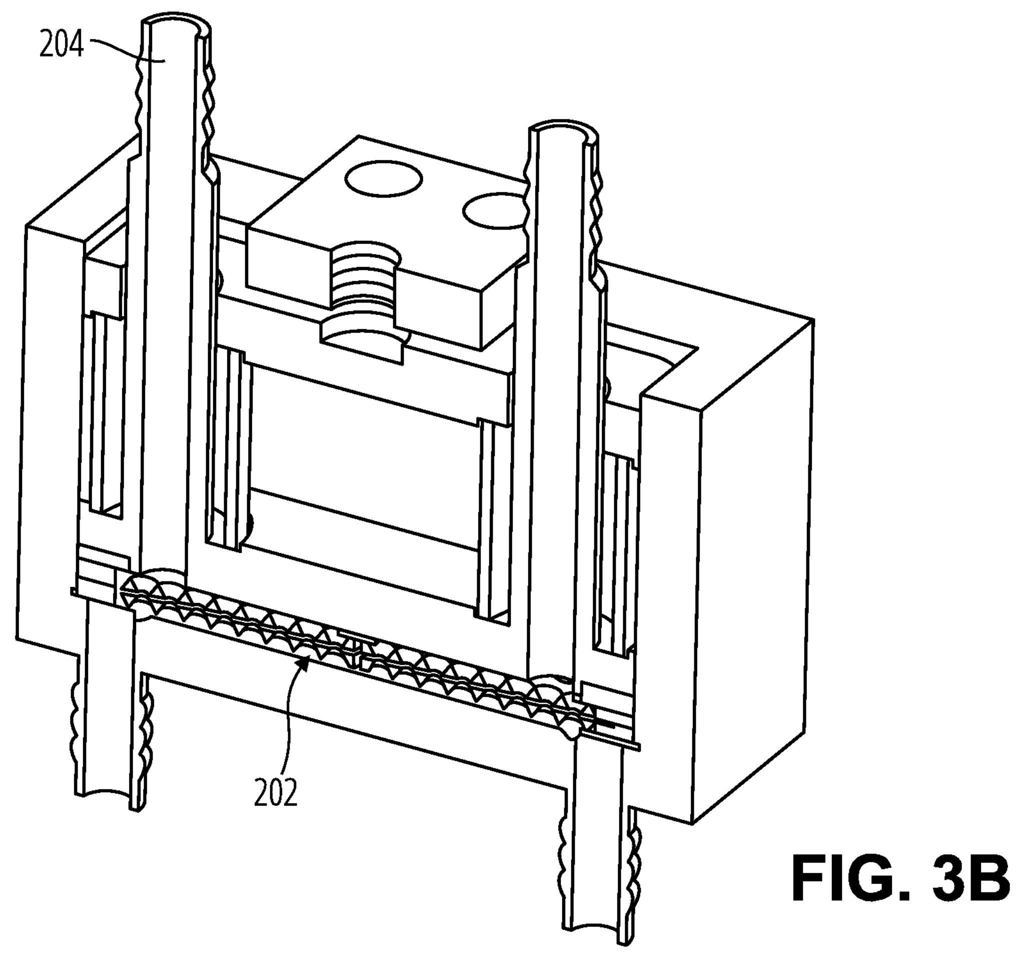
FIG. 3B depicts a perspective view of an electrolytic cell in accordance with one embodiment.

FIG. 3B depicts a perspective view of another configuration of the electrolytic ozone cell 106 in accordance with one embodiment, wherein the flow passages 204 are arranged perpendicular to the membrane 202.

Figure 4:
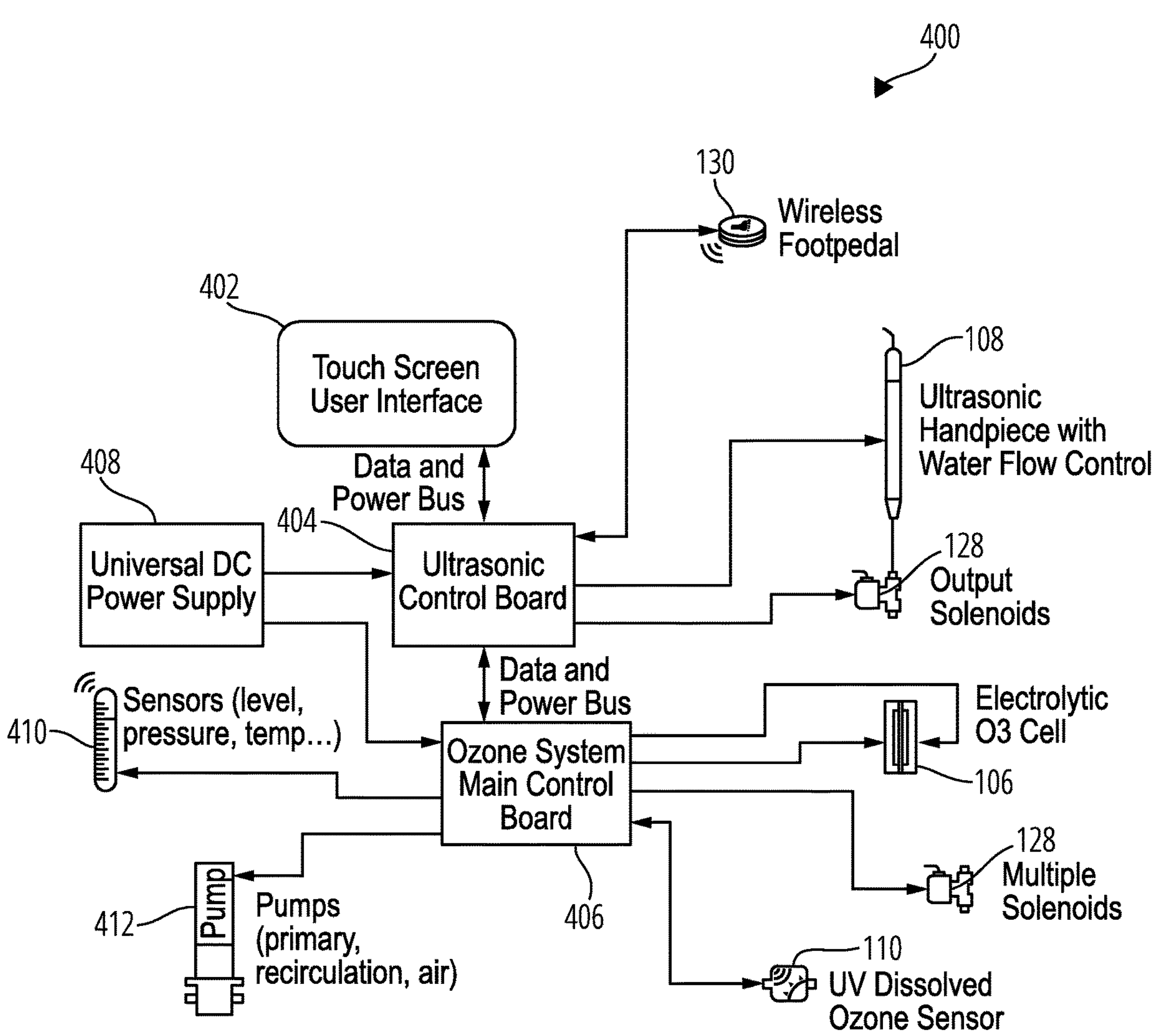
FIG. 4 depicts a block diagram of a system in accordance with one embodiment.

FIG. 4 depicts a block diagram of an interactions 400 between components of the aqueous ozone ultrasonic scaler system 100 in accordance with one embodiment. The interactions 400 comprises communications among an electrolytic ozone cell 106, an ultrasonic handpiece 108, a uv sensor 110, a solenoid 128, a foot pedal 130, a user interface 402, an ultrasonic control board 404, an ozone system main control board 406, a power 408, a sensor 410, and a pump 412. The components for a part of all of the aqueous ozone ultrasonic scaler system 100 of FIG. 1. The ultrasonic control board 404 and the ozone system main control board 406 are included in or form one or more control units for controlling the interactions 400 in the aqueous ozone ultrasonic scaler system 100.

Figure 6A:
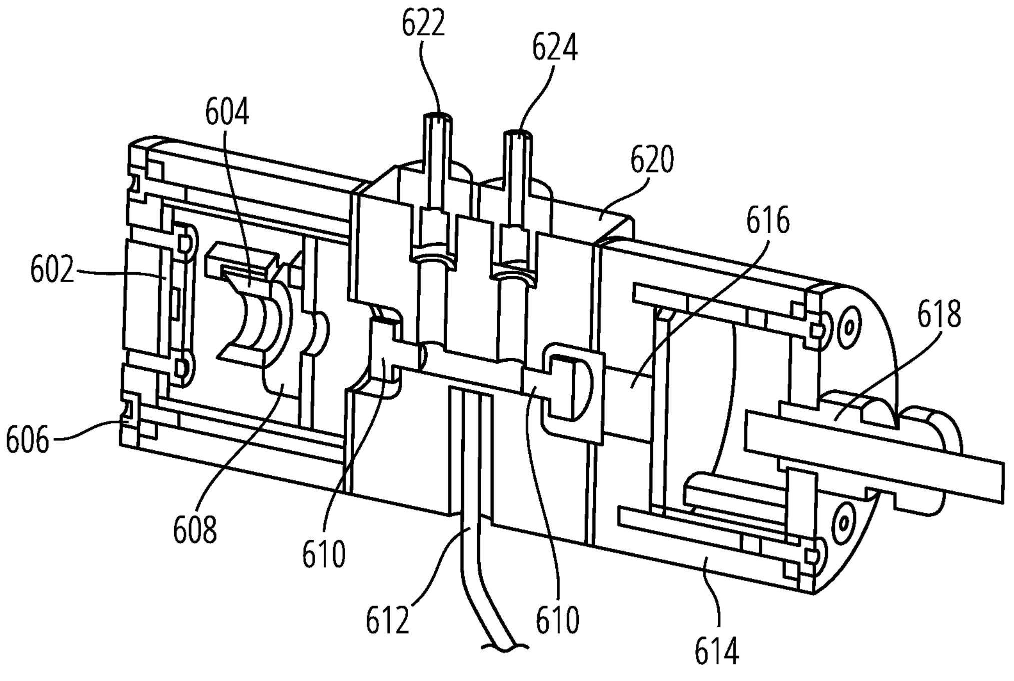
FIG. 6A depicts a perspective view of an ultraviolet (UV) sensor in accordance with one embodiment.

FIG. 6A depicts a perspective view of a UV sensor 110 in accordance with one embodiment.

The UV sensor 110 comprises an LED with temperature sensor 602; a mount 604 to allow the addition of a lens; a lid 606 holding mounting points for optical and electronic components to allow for easy removal and maintenance; said lid providing heat sinking, a monitor photodiode (off axis) 608 to allow for the compensation of changing LED output/intensity with time, said monitor photodiode having a temperature sensor; and a stepped window 610 made of sapphire to allow for light transmission, resistance to chemicals and mechanical toughness with minimal flow voids. The UV sensor 110 also has a temperature sensor hole 612 to enable thermal expansion if necessary, an anodized aluminum tube 614 that is, for example, externally threaded and screwed in to provide pressure on window holding optical components and printed circuit boards (PCB), a measurement photodiode (on axis) 616 (detector) with temperature sensor to allow for compensation for photodiode (PD) sensitivity changes with temperature, a routing gromet 618, a Kynar Polyvinylidene fluoride (PVDF) block manifold 620 for ensuring accuracy of the light path and ease of integrations and, and an input kynar barb fitting 622 for receiving water whose ozone level is to be measured, which is output through the output kynar barb fitting 624.

Figure 5:
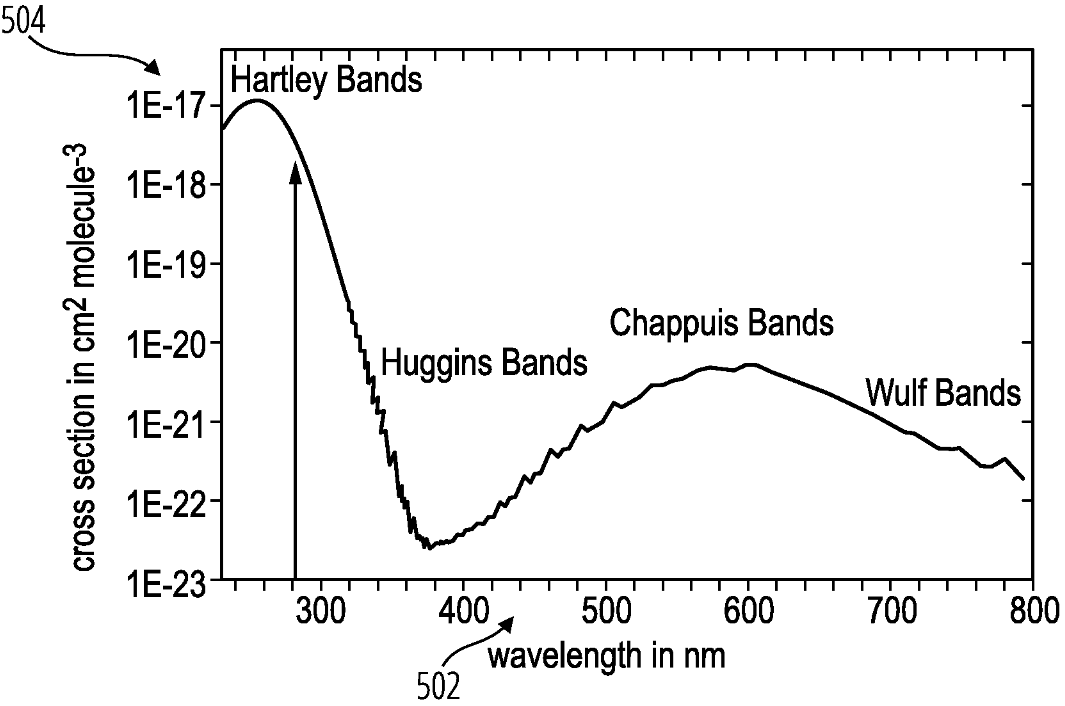
FIG. 5 depicts a chart in accordance with one embodiment.

To maintain both safety and efficacy the aqueous ozone ultrasonic scaler system 100 is configured to measure ozone directly in the water by measuring the absorbance of ultra-violet light. The UV Sensor 110 operates on the principals of light absorption and utilizes an ultraviolet light emitting diode (UV LED). Light is absorbed strongly by ozone in the ultra-violet region of about 280 nm as shown in FIG. 5. 280 nm LEDs may be selected as it is less expensive than 260 nm LEDs (260 nm is where the absorption peak is) and still gets absorbed enough to be detectable. Of course, the selection is not limited to 280 nm LEDs.

The light spectrum for ozone absorbance is shown in FIG. 5. The sensor for measuring dissolved ozone utilizes this phenomenon. The principle is absorption of light by ozone. E.g. the more ozone produced, the lower the UV signal that will be detected. The light arriving at the measurement photodiode (on axis) 616 is mathematically described by the Beer-Lambert law, which relates the attenuation of light to the properties of the material through which the light is travelling.

$$V=V_o[T_{led}]\cdot\text{loss}\cdot e^{-\sigma[\lambda],x[T],concentration}$$

The light that projects through a column of water is expressed as the voltage V at the output of an amplifier of the detector (measurement photodiode (on axis) 616). $V_o$ is the voltage from the detector when there is nothing absorbing or scattering the light. This depends on led brightness which changes with the temperature of the LED $T_{led}$. The system will monitor continuously two parameters, the output from the led and the temperature of the led. $\sigma[\lambda]$ is the absorption cross-section (in units of area). V is the signal voltage which represents the light detected. The detector voltage depends on its temperature, so the UV sensor 110 is capable of measuring and compensating for temperature effects. Its value depends on the LED wavelength $\lambda$ which in turn is altered by temperature changes. This change is predictable and can be compensated for using additional circuitry and software. $x[\lambda]$ is the distance that the light travels through the water containing dissolved ozone. This is the path length. The path length/absorption cross-section has the potential to be altered by temperature changes due to material expansion. This change is minimized by material choice and any drift is either compensated for or merely accepted. These values can vary from unit to unit, and thus can be remedied by using a calibration method as part of the final test procedure in manufacturing, the calibration can be done using a known "concentration" of dissolved ozone to give provide a value for the combined constants ($-\sigma\cdot x$). This value is referred to as the "calibration constant". The system is capable of correcting this constant for changes caused by temperature, by knowing how it varies with temperature and adjusting it with ambient temperature during operation. Loss is caused by window contamination or anything which gets in the way of light. This can be evaluated as a more frequent zero test when there is pure water in the flow path x. It is assumed that there is no significant absorber at this wavelength and experiments have shown that peroxide, for example, has an insignificant effect at this wavelength. During the system start-up at, for example for each day, the catholyte from the previous day is circulated through the UV sensor, the catholyte will be free of ozone and provides a reference fluid for zeroing out any errors related to the optical path (i.e. residue, surface build-up that reflects and absorbs photons offsetting the ozone measurement). To reduce LED heating, and to remove 'dark current' the LED is pulsed, measuring in both the 'on' and 'off' states. The pulses last, for example, approximately 3 ms 'on' 3 ms 'off', they can be as short as, for example, 200 microsecond and as long as 10 seconds. The timing is software controlled, however additional circuit elements can provide hardware-based pulsation with picosecond repeatability and accuracy. The 'on' value for each flash has the corresponding 'off' value subtracted from it (allowing removal of transient lighting variation), and the resulting value averaged over 100 flashes, or as little as 10 flashes or more than 100,000 flashes.

The use of light is a non-contact approach to measuring dissolved ozone and avoids introducing contaminants in the waterline that would be associated with electrolytic ozone sensors that must contact the water.

Figure 6B:
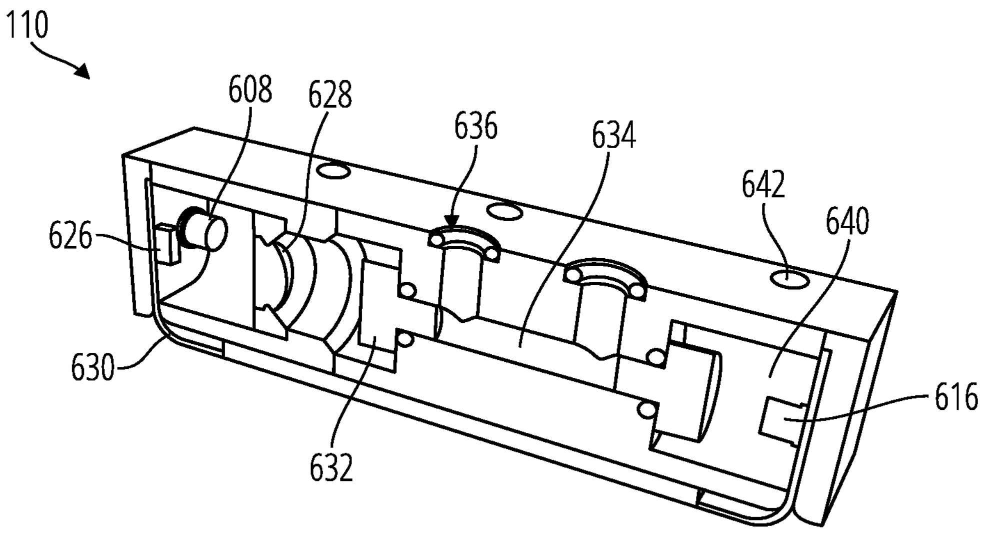
FIG. 6B illustrates a cross sectional view of an ultraviolet (UV) sensor in accordance with another embodiment.

FIG. 6B shows a uv sensor 110 according to another illustrative embodiment. Said uv sensor 110 may be configured with an outer housing that allows it to be compatible with a manifold (not shown) of the aqueous ozone ultrasonic scaler system 100. A plurality of manifold mounting points 642 allow the sensors to be attached to the manifold. The uv sensor 110 includes a monitor photodiode (off axis) 608 to monitor an intensity of light projected by the UV LED 626. A measurement photodiode (on axis) 616 is located on an axis of projection is configured to measure an amount of uv light returned which indicates a concentration of ozone in the water passing through the water column 634 from a fluid port 636. A collimating lens 628 collimates the uv lights towards the measurement photodiode (on axis) 616. The measurement photodiode (on axis) 616 is coupled to the housing 640 and connected to the flexible circuit 630 such that movements of the flexible circuit 630 during, for example, manufacturing, do not displace the measurement photodiode (on axis) 616 from the axis. The flexible circuit ideally has on board electrical connections 638 that allow the bringing of power, analog signals, temperature, and digital communication lines to the UV sensor 110 from an external/main control circuit in order to allow local measurements and calculations which prevent or substantially eliminate noise that would otherwise be generated in a sensor that does not possess local measurement and local calculation abilities.

Figure 6C:
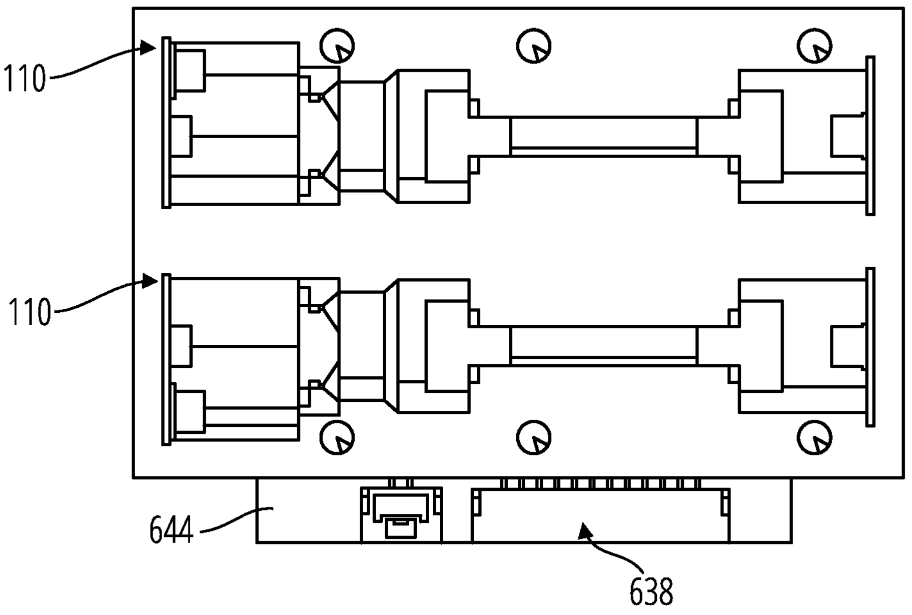
FIG. 6C illustrates a perspective view of an ultraviolet (UV) sensor in accordance with another embodiment.

In another illustrative embodiment, as shown in FIG. 6C a plurality of uv sensors 110 are combined in myriad configurations, each sensor being configured to be used during a corresponding switching configuration of the electrolytic ozone cell 106, for example, one uv sensor 110 may be used during and anode/cathode configuration and a different uv sensor 110 may be used when the configuration is switched by a reversal of polarities of the electrolytic ozone cell 106 to a cathode/anode configuration. A rigid PCB 644 may be a sub-part of the flexible circuit 630.

The integration into an ultrasonic dental scaler of an aqueous ozone generator equipped with closed loop control of the ozone concentration requires the reduction of key components and integration into a fluidic manifold. The UV sensor 110 used to monitor the concentration of ozone is a key component that is required on both sides of the system, catholyte and anolyte, to support daily polarity switching. Two small sensors or a single sensor with two channels is required. Alternative approaches include using 4 3-way valves to divert the recirculation water loop through the sensor, the valves would switch depending on which side of the system was producing ozone.

As the ozone is produced in an electrolytic cell its production can be increased or decreased based on the level of DC current flowing into the cell. The information provided by the UV sensor provides the control loop with a measurement of the ozone concentration in the water being recirculated in the system. The aqueous ozone travels from the cell into the gas separators and then from the gas separators into the UV sensor. The gas separators assure that the water flowing through the UV sensor is clear of bubbles, bubbles will block the light in the UV sensor producing noise in the measurement. Static bubbles that form within the fluid paths while the system is off have to be flushed out of the UV sensor. To achieve a clear column of water the fluid channel through the system is designed to avoid Eddie currents and voids that would reduce flow velocities and prevent bubbles from being carried away in the flow stream.

The manifold compatible UV sensor has two fluidic ports that are connected to the manifold during the assembly of the UV sensor to the manifold. An interfacial seal between the body of the UV sensor and the manifold form the fluid connection. Water flows out of the manifold, into the UV sensor, and back out of the UV sensor into the manifold. The fluid path is oriented to avoid bubble entrapment, therefor its preferable to locate the UV sensor on the bottom of the manifold so that gravity can assist with the flushing of bubbles. The sapphire windows at each end of the water column must be exposed to the fluid flow so that bubbles and debris are easily removed by the flow of water through the sensor. Mounting the sensor to the bottom of the manifold more readily supports the integration into an ultrasonic scaler by designing the sensor with a low profile which supports the need to minimize the scaler height, a requirement for installation in a dental operatory.

The manifold compatible UV sensor 110 may be designed for ease of assembly. The sensor provides a sealed fluid path capable of transmitting ultraviolet light through a water column 634. At both ends of the water column 634 are electro-optical components that are aligned to optimize the signal to noise ratio. Mounting the UV LED 626 and the measurement photodiode (on axis) 616 on flexible circuits 630 mechanically decouples these electro-optical components from any rigid PCB that integrates all the electronics for controlling the LED, powering and amplifying the photodiodes, digitizing, and analyzing the analog photodiode signals. A sensor circuit includes a microprocessor to process algorithms that use the analog voltages from the detector photodiode and monitoring photodiode together with calibration and loss values to calculate the ozone concentration. By maintaining a local microprocessor, the ozone concentration can be transferred digitally over, for example, an 12C bus to a central microprocessor responsible for controlling the entire aqueous ozone system, ultrasonic scaler, and user interface. Processing the analog signals close to the photodiodes reduces the potential for electrical noise coupling as analog signals lines can be kept short and shielded from external noise sources (e.g. pump motors, solenoids, power supplies, DC regulator, touchscreen electronics). The UV sensor 110 designed with full integration of both the analog signal processing, analog-to-digital conversion, computation, and digitization of the ozone concentration also simplifies the factory calibration routine. UV sensors 110 can be calibrated and inventoried as completed modules. The ultrasonic scaler provides a DC power source and a connection over I2C bus to access the sensor information. The sensor can provide serialization information, ozone concentration, sensor health diagnostic information related to loss information, temperature values for the UV LED 626 and photodiodes as well as firmware version and calibration details. This module approach directly supports product service as sensors can be swapped out without the need for calibration once installed into the aqueous ozone ultrasonic scaler 706.

Turning back to FIG. 1, the gas separator 116*a* and gas separator 116*b* will now be further described. In the aqueous ozone ultrasonic scaler system 100, there is a gas headspace in equilibrium with the ozone containing water. Bubbles are generated at the anode side 124, due to the locally high gas concentrations generated there. The bubbles coalesce in flow to form a headspace 136, and in general this headspace 136 in a well-mixed system will be approximately in equilibrium with the water. Controlling the volume of the headspace 136 and entrained gas in any outlet is important. Conventional ozonation systems use a venturi to dissolve ozone gas into water flowing through a pipe, however this approach does not prevent undissolved gas from traveling to the dental handpiece and does not support a system that uses low flow rates, less than 40 ml/min, and typically less than 20 ml/min, as these flows lack the energy (fluid velocity and volume) to generate adequate ozone concentrations by pulling gas into the flow path.

As part of the optimized flow system, a bubble-free portion of the flow is directed to the output of the flow system into an ultrasonic handpiece 108 in response to user demand. It is also possible to provide some buffering or averaging of both ozone concentration and system pressure fluctuations. Furthermore, pumps operate most efficiently in the absence of bubbles. Bubbles are present in the flow system when the ozone-generating cell is operating, and so continually separating the bubbles from the flow produces bubble free ultrasonic scaling lavage preventing the gas that escapes from the lavage from entering into the patient's oral cavity. At a minimum, this gas separator also provides a buffer reservoir for ozonated water, a gas headspace 136 buffer volume, a region for water level sensing, and a connection point for multiple gas and water connections. In an illustrative embodiment, the following functions are combined in a single aqueous ozone ultrasonic scaler system 100, including: (i) employing a plurality of recirculation loops 132 and corresponding gas separators, such as two recirculation loops 132 each having a gas separator that separates the water volume such that the system polarities can be alternated to provide fast production of aqueous ozone water and extend the shelf life of the electrolytic ozone cell 106 (while a gas separator 116*a* at an anode side 124 of the electrolytic ozone cell 106 may be in use, another gas separator 116*b* at the cathode side 126 may not be in use and a switch of the polarities may ensure that gas separator 116*b* that was at the cathode side 126 is now at an anode side 124 and is therefore ready for operation). The polarity switching can happen daily, for example, and will keep the cell healthy so that it maintains good performance, namely its ability to reach a target concentration in a short time (for example, in 30 seconds) and maintain that concentration during scaling. During scaling the water in the system is constantly diluted as aqueous ozone exits the handpiece and fresh water is pumped into the system. To maintain levels in the separators the ozone concentration is diluted requiring the EO cell to turn on and maintain concentration. Another important reason for polarity switching is to eliminate the need for daily system flushing, which would take time and waste water. Without daily flushing (for example) of the catholyte water, it would not get emptied or replaced. The polarity switching there ensures that the catholyte side is changed over to the anolyte side and the water is then ozonated and replaced during scaling, (ii) removing entrained gas from an output of the gas separators to provide bubble free ultrasonic scaling lavage and prevent gas from escaping from the lavage into a patient's oral cavity, (iii) providing the UV sensor 110 with a clear water sample (bubbles reflect and diffract the UV light to produce erroneous signals measurement. Although bubble-generated-light attenuation-signals could be averaged out, the performance of the electrolytic ozone cell 106 is enhanced with a clear water sample), (iv) providing pressure smoothing in circuit, (v) reducing concentration fluctuations at output by control of the electrolytic ozone cell 106, (vi) lengthening timescale of control circuit (reduced bandwidth), (vii) making parameters of cell flow of the electrolytic ozone cell 106 independent of output flow of ozonated water into the ultrasonic handpiece 108 through the use of a controlled output of the gas separators, (viii) providing a headspace 136 for the separation and collection of excess gas from the system, (ix) smoothing system pressure fluctuations, (x) isolating water reservoir from headspace connections e.g. to ozone destroyer 114.

The system topology combines a through-flow with an internal recirculation loop 132 to reconcile the distinct flow conditions required for optimum electrolytic ozone cell 106 and for ozonated water delivery. The cell operates best at near steady state with a high-water velocity across the electrode plates, for both thermal and gas-bubble transport reasons. The output flow must respond to user control and can be highly intermittent.

Bubbles have a natural rate of rise in water, and to allow flotation to efficiently remove bubbles from a flow, there must be a portion of the flow with a free surface in which the residence time is greater than the maximum rise time of a bubble to the surface. The maximum rise time is a function of the bubble size, and the height it has to rise to reach the surface. In an illustrative embodiment, the design feature of the separator can be that the inlet flow is directed to the free surface of the reservoir, but from below so that it does not cause turbulent bubble entrainment of additional gas from the headspace into the liquid. The liquid level is managed by the system through the use of a water level sensor such as sensor 102 to maintain the no-entrainment condition during normal operation.

In another illustrative embodiment, the flow path from the electrolytic ozone cell 106 to the separator maximizes bubble coalescence and minimizes bubble fragmentation, to ensure that the average bubble size is as large as possible. Larger bubbles rise faster and so allow better separator performance or a smaller separator working volume to be used.

In another illustrative embodiment, incoming flow of water into the separator is baffled and conditioned to minimize jetting and reduce the scale of turbulent eddies in the incoming flow region as described hereinafter.

In another illustrative embodiment, the liquid volume of the separator is provided with baffles spaced to suppress bulk overturning flow in the chamber, hence reducing the possibility of bubbles being carried downwards towards the exit ports by a relatively low energy circulating flow. The design of the inlet and baffles is such as to create as much as possible a uniformly slowly moving downward flow across the whole area of the chamber. Vortices in the flow have to be smaller than the spacing of the baffles, and this spacing can be adapted to suit the chamber shape and the placement of the inlet and exit ports.

The separator chamber is characterized by a cross sectional area which satisfies the following relationships: (i) Bubble rise time<residence time of water in reservoir; (ii) Velocity of bubble rise (for target diameter cutoff)>downwards average velocity of flow in chamber; (iii) The bubble behavior and flow conditions in the separator are determined by several interacting design parameters; (iv) Bubbles penetrate as little as possible into the water in the chamber (There is the balancing of the removal of bubbles and the mixing of freshly ozonated water with the separator volume that is being diluted by fresh input water. If he bubbles coming out of the recirculation loop input are allowed to penetrate the full volume of the liquid in the separator there is a good chance that they will be pulled into the recirculation loop exit port or fluid discharge port. So the bubbles are directed towards the gas-fluid interface so that they can be released into the gas side and not enter into the discharge line or re-enter the recirculation loop). Incoming flow is directed at the free surface, and overturning circulation that carries bubbles down into the water is suppressed; (v) The diameter of vortex flows in the chamber is set by the lateral dimensions of the flow volumes. Subdivision of the volume should be so as to limit vortex size and hence penetration depth of the bubbles; (vi) The average flow velocity in the chamber is less than the rise velocity of the smallest bubbles for which removal is required; (vii) The velocity variation across the chamber is as low as possible, i.e. it is approximated to a laminar plug flow profile; (viii) The exit points from the chamber, particularly that for the delivery flow path, are placed where the likelihood of an excess downward flow velocity is minimized. This minimizes the chance of any bubbles reaching the exit point; (ix) The exit flow port is baffled such that it draws flow relatively uniformly from across the area of the chamber.

A chamber satisfying the above conceptual design rules can be cylindrical or rectangular in section. It may have an aspect ratio (height/width)>1, and preferably >2. A subdivision of the chamber can be in different forms, e.g. square or circular or hexagonal, without affecting the function, and the separation elements can span from the base of the chamber to the free surface or slightly away from those surfaces, without limitation. The height of the gas headspace 136 above the free water surface as determined by other factors and can vary widely without affecting the bubble separating function of the water volume. For use with ozonated solutions, preferably the wet surfaces are all comprised of ozone-inert materials such as fluoropolymers, or substrates coated with a protective layer that does not react significantly with ozone. Associated with the chamber may be level sensing means such as sensor 102. The structure of the chamber can be adapted to allow level sensing by e.g. capacitive sensors or by other depth sensors integrated into the chamber, without affecting the function.

The combination of a compressible gas volume in fluidic connection with a reservoir volume 138 results in a smoothing of pressure pulses in the circuits connected to the volume. In this system, this smoothing effect applies to incoming flow from an air pump **118*a* (or air pump 118*b*), to recirculating flow through the reservoir volume 138, and to flow out to an outlet 140**. If there is an applicable criterion for allowable pressure pulses in any of these flows, and a known source of pressure pulsations e.g. a pump or a valve, the volume of fluid and gas in the chamber can be adapted to provide the necessary filtering of pressure variation vs time. The specific values of volume required also depend on the inertance of the associated pipe flows, and the elasticity of the pipes. In an illustrative embodiment, the pipes are negligibly elastic, and the pressure-smoothing optimization is derived by calculation of the flow inertance and the chamber volumes.

The gas separator provides a reservoir volume 138 of aqueous ozone to draw from during the scaling procedure, rather than drawing the flow directly from the electrolytic ozone cell 106. The system can use a control setpoint for the ozone level in the chamber, which is efficiently circulated and mixed by the recirculation through the cell independently of the output flow. Thus, an ozone sensor control loop can be embodied without risk of error from uneven flow patterns through a sensing element, or variable ozone decomposition during periods of low or no flow through a sensor. Having a reservoir of aqueous ozone minimizes the variation in ozone levels flowing out to the ultrasonic handpiece and decouples output flow rate from the instantaneous electrolytic ozone cell 106 operating parameters or the momentary operation of a drive pump. As fluid being dispensed as aqueous-ozone-ultrasonic-lavage leaves the system via the ultrasonic handpiece 108 it must be replenished. Fresh water enters the system to make up for the output flow in order to maintain the water level in the separator. Fresh water mixes with the fluid in the separator and recirculation loop causing some dilution which is recovered by the electrolytic cell under the control of the ozone sensor. Preferably, the time constant of the control loop is short compared to the usage timing of the system but is not required to compensate for every momentary fluctuation in operating conditions, as these are naturally smoothed by the mixing process in the chamber and flow loop.

Because there is a separator volume the system will need to charge this volume of water at startup before reaching the desired ozone concentration. The target concentration level can be achieved by driving a specific current over a period of time, for instance 500 ma for 2 minutes, or using a closed loop controller that monitors the UV sensor to determine the level of dissolved ozone in the separator and recirculation path.

To improve the efficiency of the electrolytic ozone cell 106, bubbles formed at the electrolytic cell triple phase boundary are detached from the electrode surface to prevent them from reducing the effective working area. To achieve this the recirculation flow and electrolytic cell flow channel are tuned for high flow velocity at this surface. If the output flow were directly passing through the cell to the output, even with an intervening buffer volume, then the cell velocity would be varying depending on the output flow demand, making it impossible to fully determine the instantaneous operating conditions in the cell, and also requiring matching flow rate modulation of the cathode side flow rate to maintain desirable pressure balance across the electrode and membrane assembly. To dynamically modulate both flow paths in this way places a severe control burden on the system as a whole. Furthermore, below a threshold flow velocity, either cell heating or failure of bubble removal would become a risk, with the further need to modulate cell current in response not only to instantaneous output ozone level, but also in response to the thermal limitations of the electrode assembly at low flow. The system comprises intersecting flow paths which simultaneously solve many of these problems, with the use of the gas separator component as an element that allows the combination flow path to be implemented and to meet all of the system requirements. The recirculating flow rate between the reservoir volume 138 and electrolytic ozone cell 106 can be independently set to provide optimized cell operating conditions of high flow velocity and stable conditions, whilst also allowing the electrolytic cell flow channel to provide refill and output flows with appropriate rates and pressure characteristics.

There is a significant pressure drop in the electrolytic ozone cell 106 when operated at a high flow velocity and with a narrow flow path. The system design makes this pressure drop internal to the recirculation loop, whilst not affecting the apparent pressure drop in the through-flow pathway. Thus, it is possible to further optimize the system than if the separate pressure requirements were both applied to a common flow path. In an illustrative embodiment, the average working pressure of the system as represented by the gas separator is set to the working pressure of the instruments attached such as the ultrasonic handpiece 108. The required additional pressure to drive the flow through the electrolytic ozone cell 106 is not in series with this pressure, but only appears in the connection between the recirculation pump and the electrolytic ozone cell 106.

Figure 13A:
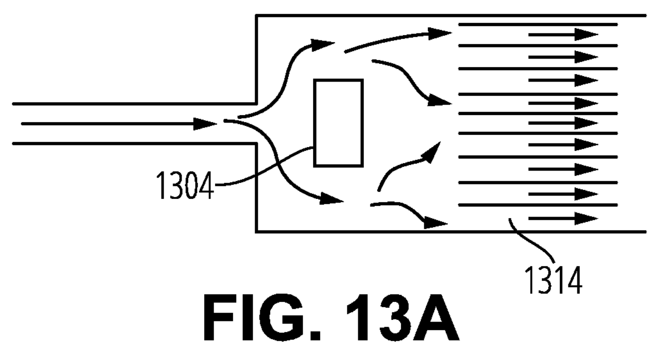
FIG. 13A depicts a flow pattern in accordance with one embodiment.
Figure 13B:
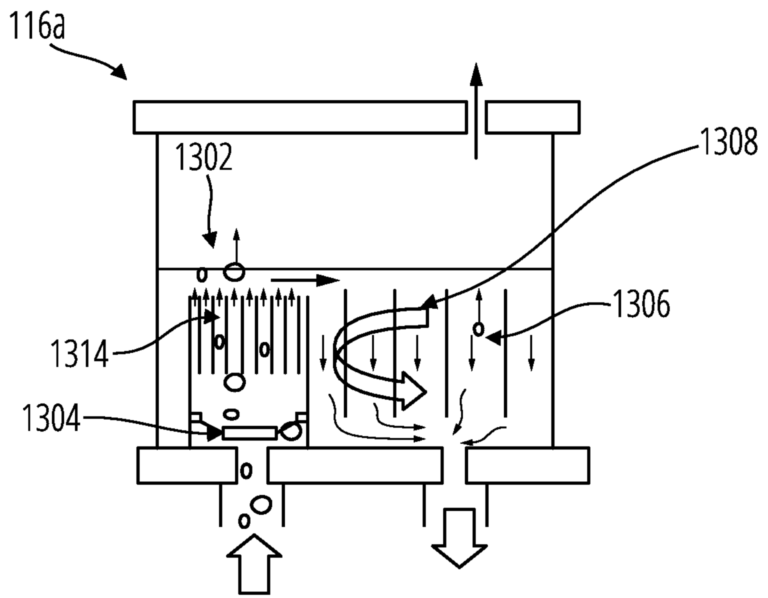
FIG. 13B depicts a flow pattern in accordance with one embodiment.
Figure 13C:
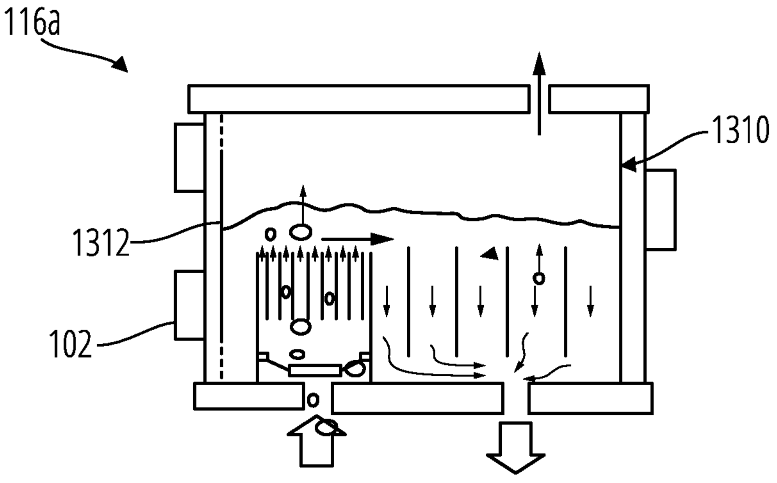
FIG. 13C depicts a flow pattern in accordance with one embodiment.

The inlet 142 to the gas separator(s) greatly reduces jet turbulence & allows main volume of the gas separator to operate in a calm flow pattern due to the use of inlet baffle 1304 which immediately spreads flow as shown in FIG. 13A. The combination of the inlet baffle 1304 and tube array 1314 slows, and controls flow into the separator. The challenge is to slow the jet speed from that in the inlet pipe, in a short distance. Simply increasing diameter does not work due to flow separation and uneven velocity profile. Even a slowly tapered expansion does not prevent this mixing. The basic concept combines an obstacle to divert the jet to radial flow, preventing separation, followed by a "laminarising" section packed with narrow tubes to enforce plug flow at a low average velocity. Testing has shown that a 1 cm diameter works easily up to 1000 ml/min. As seen in FIG. 13B, most bubbles escape at the surface 1302 and chamber baffles 1308 suppress gross overturning circulation with the bubbles rising faster than water flows down 1306. As shown in FIG. 13C the solid middle portion 1312 of integrated tube 1310 prevents surface disturbances affecting sensors 102. The integrated tube 1310 has openings all around at a top and bottom portion for water and gas level equilibration with the central region.

A mean downward water velocity is less than the upward bubble velocity for all bubbles of interest, so that they can escape to the headspace. Small bubbles rise much slower than larger ones, so the critical diameter can be found by equating water velocity and rise speed using established relations.

In a non-limiting embodiment, for very small bubbles the a velocity of the bubbles can be represented by the Hadamard/Rybcynski relation as velocity $V=\rho\cdot g\cdot d\hat{}2\cdot\mu$ for 0.2 to 2 mm bubbles an alternative is V (m/sec)=120*d(m), wherein $\rho$ is the density of fluid, g is the gravitational acceleration, d is the diameter of bubble and $\mu$ is the liquid dynamic viscosity.

Further, for very small bubbles there is a regular relation between size and speed as well as temperature and ionic strength effects on the speed. The temperature and ionic strength effects may however be minimal.

An analysis gives example values for an area equivalent to a 3 cm diameter separator (the actual inside diameter is 3.3 cm, minus the inlet tube area gives this net area for flow).

Flow=500 ml/min=8.33 ml/sec. Area=7.1 cm2 Downflow speed~1.2 cm/sec. Bubble size with Vrise=1.2 cm/sec is about 100-140 um. With the separator flow uniform, all bubbles larger than ~100 um will escape. A fast jet inlet flow drives circulating vortices much faster than the average flow, so this compromises the separation performance. There is not enough volume for turbulence to dissipate the energy. Using a calm inlet, and some further plug-flow enforcing baffles in the main chamber, one can aim for near-theoretical separation performance in the same chamber volume.

Further illustrative embodiments to improve performance include a larger diameter flow spreader on the inlet, for example, of about 15 mm, and the addition of a "jet baffle" at the inlet. Also, larger laminarising tubes in the inlet in order to reduce bubble fragmentation and a smaller diameter (e.g. About 5 mm) tube packing in the main chamber volume, to further dampen vortices. It is envisioned for the inlet flow to be prevented from "short" circuiting the packing and reaching the recirculation outlet.

In order to deliver aqueous ozone to the ultrasonic handpiece 108 the system pressure (which can range from 15 to 40 psi but more typically 22 psi) requirement is determined by the pressure required to generate as much as about 65 ml/min or less, but more typically 25 ml/min output flow rate. Some ultrasonic inserts are designed with small fluid paths through the insert tip. These fluid paths can be less than 0.020 inches and typically smaller than 0.015 inches. The system pressure also effects the gas solubility rate for ozone an important factor to consider for charging the system to the desired concentration quickly at start-up. Pressure is generated in the system by the pumps (air pumps, the primary water pump) and the gas generated by the electrolytic ozone cell 106. The air pumps are used primarily at startup, for periods of high flow output that may require additional input to maintain system pressure to deliver a continuous flow rate, and can also be used for purging the aqueous ozone ultrasonic scaler system 100 for long term storage and shipment without water being stored in the gas separators. The primary water pump **118*c* fills the system and gas separators and it also adds fluid to the system while the system is operating at system pressure, about 22 psi, but can range from, for example, 15 to 40 psi, and can even be operated below 15 psi and more than 40 psi. As the electrolytic ozone cell 106 adds gas to the system the system pressure will continue to increase, the system pressure can be controlled through pressure regulation. Electronically controlled through valves 120 that are opened and closed by software based on the input from a pressure transducer. In an illustrative embodiment, the gas in the buffer volume 134 can be released by two valves 120 in series, the first would open and discharge a small volume, and then close and a second valve 120 would open to discharge the small volume through an ozone destroyer 114 which converts the ozone gas into oxygen gas. This valve toggling prevents a rapid drop in system pressure. A mechanical method for limiting and controlling the system pressure is to release the gas in the headspace of the separator via a pressure relieve valve. Pressure relief valves utilize a seal and spring pressure, opening and venting only when the system pressure exceeds the pressure on the seal generated by the spring force. A pressure relief valve with quick action and very low mechanical hysteresis will provide a steady up level system pressure. A pressure transducer can be used in conjunction with the system pumps to raise the system pressure to support the desired output flow rate and gas solubility. In addition to these pressure control means are level sensors 102 that maintain fluid level in the separators. Maintaining the proper fluid level controls the volume of the gas head space and prevents a rapid change in the head space volume which would impact the system pressure. An important advantage of the aqueous ozone ultrasonic scaler system 100** architecture over conventional water ozonation systems is that it has the ability to go from no dissolved ozone to fully charged in, for example, less than 3 minutes with the potential to achieve full charge in under 30 seconds.

In using the aqueous ozone ultrasonic scaler systems 100, the following steps may be undertaken. The air pump **118*a* on the gas side is turned on to charge the system pressure. Water from the closed system container is pumped into the system until the level sensors 102 reach their preset volume. In an illustrative embodiment, these steps happen in less than 10 seconds with the potential to reach presets in less than 2 seconds, bringing the system fluid and operating pressure up to their desired levels. (The fluid level in the system would be required to fill the fluidic path and add enough volume to the gas separator to create a water reservoir and gas head space. The gas separators can, in an illustrative embodiment, be filled, for example 20 to 80% with water, or even typically 40-60%, or just above the baffles in the gas separator. The pressure in the system is increased from near zero psi. Some pressure is added to the system by pumping in water reducing the gas volume, however the vent solenoid valve is typically help open to more rapidly fill the system with water. Once the desired water level is reached the air pump is activated to quickly charge the system pressure to 15 to 40 psi, typically 22 psi.) At this moment system recirculation pumps turn on and drive current is delivered to the electrolytic ozone cell 106. In an illustrative embodiment, the electrolytic ozone cell 106 may be powered at 1.1 to 7 times its normal operating current during the initial charging of the aqueous ozone ultrasonic scaler system 100 in order to enable rapid system charging. The recirculation pumps may also operate at a higher duty cycle or voltage increasing the recirculation rate to help pull gas from the electrolytic cell quickly so that small gas bubbles are quickly swept away from the triple phase boundary of the cell membrane-electrode interface. These small bubbles provide more surface area compared to larger bubbles that form from smaller bubbles combining or from the delay release at the surface of the cell triple phase boundary. The gas from the electrolytic ozone cell 106 is more rapidly dissolved into the recirculating water because of the higher system operating pressure. Ozone solubility in water is dependent upon the temperature of water, concentration of ozone gas being dissolved, and pressure in the system containing the recirculation water and ozone gas. Higher pressures equate to higher dissolved ozone levels. In an illustrative embodiment, by operating at 20 to 24 psi above one atmosphere over twice the amount of ozone can be dissolved into the systems water. Entrained gas is separated from the recirculation loop and then sent through the UV sensor 110. The UV sensor 110 monitors the startup routine and enables a closed loop controller to achieve a steady state condition returning both the electrolytic ozone cell 106 and recirculation pumps to normal power levels. Limiting higher current to the cell and motor to only the startup sequence improves reliability and cell membrane life. During startup the dental clinician can begin immediately filling the ultrasonic handpiece 108** with water to prepare the system, they can also start scaling or rinsing with the ultrasonic insert. However, because of the additional dilution from fresh water entering the system this may slow the overall charge time or require more power to the cell to achieve a rapid charge up.

Figure 14:
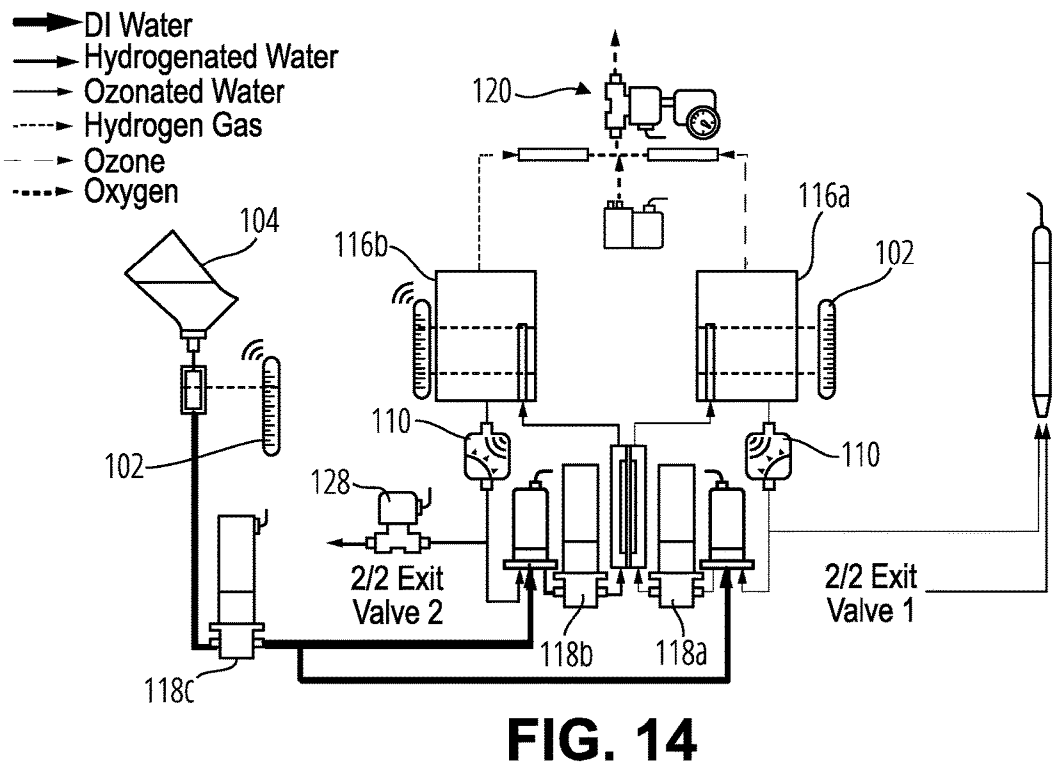
FIG. 14 depicts a system in accordance with one embodiment.

In another illustrative embodiment, the aqueous ozone ultrasonic scaler system 100 is designed such that both the cathode side 126 and the anode side 124 so are symmetrical or substantially symmetrical. In so doing the gas separators for the cathode and anode are identical or substantially identical in size, construction, volume, and their ability to separate gas bubbles from the fluid. In an illustrative embodiment, both sides have a dissolved ozone sensor, for example, each side has a UV sensor 110 (FIG. 14) one UV sensor 110 can measure two separate fluid paths each path belonging to one side, or a single UV sensor 110 that has a series of isolation valves that can redirect either fluid path of the system through the sensor to provide the system with the ability to monitor ozone gas in either recirculation loops 132. The potential to measure ozone gas in both recirculation loops 132 simultaneously or in an alternating manner could provide added self-diagnostics. By monitoring both sides a decision can be made to maintain the anode as the anode or if ozone levels are acceptably low (for example, less than about 0.2 ppm or undetectable) the system could reverse polarity. The software of the aqueous ozone ultrasonic scaler system 100 changes the polarity to the electrolytic ozone cell 106 through, for example, an H-bridge and provides output flow from an outlet 140 of whichever side of the system is producing ozone. Another benefit to monitoring ozone levels in both the anode and cathode is to monitor for gas crossover. Ozone in the cathode recirculation loop could indicate early signs of cell membrane perforation or loss of fluid and or gas seals. This type of self-diagnostic can help to both mitigate safety concerns as well as alert end users prior to a loss of functionality or performance.

The need to switch system polarity comes from a need to maintain fluid levels in the catholyte and important system characteristics related to reliability. During operation, water molecules are pulled through the membrane 202 via electroosmosis. Over time the gas separator 116*b* will increase in its fluid level (As water migrates via electroosmosis from the anode to the cathode or from fluid leakage internal to the EO cell, the catholyte volume increases). Without a drain or reason to discharge from the cathode side of the system the gas separator 116*b* will fill up and eventually need to be drained. By switching the overall system polarity daily, for example, the small increase in fluid level from a day of usage will be easily managed. The reliability requirements related to polarity switching stem from the electrolytic cell's long-term performance objectives and the need to maintain the cleanliness of the water in the catholyte without the need for special startup or shutdown process steps. An extra maintenance step would be undesirable because of the extra time involved or need for drain lines to be installed or conveniently located. Ultrasonic scalers typically sit on countertops, in cabinets, or special drawers designed for the operatory equipment. However, these locations do not provide access to a drain, therefore the system would need a waste bin to collect catholyte water at the end of a day. Or the clinician would have to purge the system of any fluid into the operatory sink by running a special purge cycle. The purge cycle would run a maintenance pump, small diaphragm air pump, that would push the water out of the system through open water solenoids out to the handpiece. During this purge cycle water would be dispensed into a nearby sink or small reservoir. During this purge the risk exists that an ozone gas stored in the head space would also be discharged from the handpiece. This would be an unwanted exposure to ozone gas. To avoid this exposure and the need to run a special purge cycle that would be inconvenient and require additional setup time, a system capable of changing polarity daily automatically refreshes and ozonates the prior day's catholyte side of the system.

Since the water in the cathode side of the system is not using during scaling it would regularly need to be replaced via an additional setup or shutdown step. This water can be replaced via a purge process requiring a small air pump that can displace the water from the cathode side of the system into a waste container, drain, or through valves ported to the ultrasonic handpiece 108. These options may require a special cathode purge step during startup or shutdown of the ultrasonic scaler. During the scaling procedure water will be transferred by pumps from a pure water source such as from a custom closed water packaging system (e.g. Spout pouch 704) that is both tamper resistant and designed with a custom fitment. The water travels through the anode side 124 of the system, ozone is dissolved into it and then it is delivered to the ultrasonic handpiece 108 as a cooling lavage for both the transducer and ultrasonic scaler tip. During startup the cathode separator (gas separator 116*b*) is filled with the proper volume of water to be recirculated through the cathode side of the electrolytic ozone cell 106 for the reduction reaction.

Alternatively, the cathode and anode can be switched, for example, on a daily basis. During off hours, for example, 12 to 16-hour periods when the system is not in use ozone will naturally decay, the half-life of aqueous ozone is typically about 20 minutes, avoiding any concern from the effects of cross-over gases. Once the ozone has decayed below about 0.5 ppm or lower the risk of back chemical reactions at the triple phase boundary of the electrolytic ozone cell 106 will be minimized. The system can safely change the polarity of the cell by switching the electrical polarity of the cell. The software drives this change in polarity such that aqueous ozone is delivered by opening the appropriate solenoid valve. By changing the polarity, the remaining cathode water from the previous day, will be recirculated through the electrolytic ozone cell 106 on its positive or oxidative anode side 124. The remaining anodic water, from the previous day, will have naturally decayed so that the ozone in the corresponding separator will have returned to oxygen and this water will be recirculated through the reductive side of the cell, cathode. Both separators will require fluid lines and solenoid valves that can deliver water to the ultrasonic handpiece 108. By switching polarity daily and only after verifying the ozone levels have decayed the cell can alternate its anode and cathode, helping to limit any fouling from deposits that typically deposit onto the cathode electrode. The membrane degradation that occurs from the interaction of ozone and other oxidative species (HO, H2o2, H3O . . . ) can be distributed over both sides of the cell extending the life of each membrane. Furthermore, the catholyte will be exchanged daily and each side of the system will be ozonated preventing stagnant water and eliminating or substantially the possibility for microbial contamination. Of course, other arrangements that prevent stagnant water, reduce ozone exposure and increase membrane 202 life can be obtained in light of this specification. The examples in this disclosure are used only for the clarity of the description and are not limiting to the illustrative embodiments. Additional operations, actions, tasks, activities, and manipulations will be conceivable from this disclosure and the same are contemplated within the scope of the illustrative embodiments.

Further, optical methods for detecting the level of dissolved ozone in water taking advantage of the ultraviolet light absorbance of ozone may require offset correction to account for changes in the mechanics and optical path (i.e. debris, aging of the UV source). By implementing a daily polarity change to the system, the previous days catholyte water, water with dissolved hydrogen, can be used for zeroing out any sensor offsets making a correction without the variable concentration of an absorbing constituent in the water.

Ozone gas is known to cause irritation of the respiratory system, thus, to prevent the patient from inhaling ozone gas an illustrative embodiment has built in control over ozone concentration and limits to ozone production. Released ozone from system is entirely comes from the delivered water flow. All the gaseous headspace ozone from the gas separator is destroyed catalytically before being vented into the local environment.

One concern for scaling with ozonated lavage is out gassing in the oral cavity (dissolved ozone diffusing from the lavage naturally creating a local environment) within the oral cavity that must be maintained. The risk of exposure can occur during a scaling procedure if ozonated water, delivered to the patient's oral cavity, accumulates and outgasses prior to being evacuated by the clinician from the oral cavity.

By fully integrating the ozone generation and control within the ultrasonic scaler electronics the exposure of ozone gas can be mitigated by monitoring the usage of the system during a single procedure providing the ozone control system with the specific mechanisms for limiting ozone gas exposure. Ultrasonic scaler parameters that may impact the amount of ozone gas released into the oral cavity include but may not be limited to, flow rate of the lavage, ultrasonic power level, duty cycle of the scaling procedure, and the type of suction used, namely high volume evacuation and/or a saliva ejector.

Ozone concentration directly determines the amount of available ozone in the lavage. For patients with healthy gums a clinician may choose to use a lower concentration of ozone, a level only necessary for suppressing biofilm growth in the system water lines, for instances 0.020 ppm to 1.0 ppm, more typically 0.5 ppm. For patients with gingivitis or periodontal disease a higher concentration may be selected by the user, 1.2 to 3.0 ppm and 3.0-6.0 ppm, respectively.

The control system may operate using a real time clock, enabling the scaler to track usage. The total scaling time per patient can be displayed and automatically reset after a period of no use, typically 30 minutes to one hour. This usage data can also be used to monitor the total amount of ozone produced and dispensed over a period of time. The system could automatically reduce the ozone concentration if an extensive period of scaling at high concentrations has been reached. As an example, Scaling times in excess of 45 minutes at 3.0 to 6.0 ppm may be found to reach the safe exposure limits for the patient.

To assure the use of suction the system can be equipped with an ultrasonic microphone. An ultrasonic microphone has the ability to detect acoustic emissions from the use of suction. If the system cannot detect the use of suction it may prevent the clinician from delivering higher concentrations of ozone. The ultrasonic microphone could be placed near the handpiece by locating it in the handpiece cable. The system housing could be equipped with several ultrasonic microphones to provide an omni directional detection capability. The ultrasonic microphone could be trained on the sound of a specific operatory saliva ejector suction and high-volume evacuation. Or the system could be preprogrammed to identify both low and adequate suction, enabling higher concentrations when selected by the clinician. High volume evacuation can remove both fluid and gas at a typical rate of 200 to 250 LPM (liters per minute), this level of suction eliminates the risk for patient inhalation of any ozone that escapes from the ultrasonic lavage prior to being suctioned out of the oral cavity.

The full integration of the ultrasonic scaler electronics and the ozone control circuitry enables the creation of control loops that take into consideration rectified diffusion and rapid decomposition. Rectified diffusion is a result of acoustic energy shearing dissolved gas out of solution as oscillatory sound waves cause bubble formation. These bubbles expand and compress with the wave of sound traveling through the solution, gas can diffuse into these bubbles and prevent their collapse, essentially liberating the dissolved gas. These small bubbles may flow through the handpiece and exit at the tip of the ultrasonic handpiece 108. Since rectified diffusion can add to the release of ozone gas in the oral cavity the concentration of ozone used for various levels of ultrasonic excitation can be directly controlled by the integration of the two electronic control circuits. Rapid decomposition is the accelerated decay of ozone to oxygen through mechanical excitation, in this instance the system could increase the ozone concentration to help maintain adequate ozone levels in the lavage so that it reaches the periodontal pocket.

Ultrasonic scalers use a lavage to cool both the transducer and the ultrasonic scaler tip. The flow rate of an ultrasonic scaler can be adjusted by the clinician, although a typical flow rate is between 15 and 25 ml/min, the system can be operated with as little as, for example, 2-5 ml/min at the low end and as high as, for example, 30-45 ml/min at the high end of the flow.

In an exemplary embodiment, the gas separator **116*a* or gas separator 116*b* provides a fluid level that can be monitored using non-contact fluid level sensing, for example capacitive or optical methods. By monitoring the level of the fluid in the anode separator the flow rate of fluid out of the system can be calculated. The system operates under pressure, typically 22 psi. When an output solenoid is opened the pressure stored in the system forces the water through the open output solenoid and into a cable of the ultrasonic handpiece 108 through a flow control and into the handpiece eventually exiting at a lavage port on an insert of the ultrasonic handpiece 108. The flow control is a mechanical device that may not communicate directly with the systems electronics. An alternative flow control could be handled via a proportional valve, servo-controlled valve, servo controlled mechanical regulator, or by simply adjusting the system internal operating pressure. As the clinician adjusts the mechanical flow control, located at the handpiece and handpiece cable interface, the rate at which the anode separator volume drops can be detected. During periods that the primary pump fills the anode separator the system software may know not to calculate the rate of water usage. During the filling time the level sensor can also be used to determine if the primary pump is operating adequately and if the water container has been emptied. If the water container is empty the primary pump will not be able to fill the anode separator. A timer will be set to provide enough time, e.g. 50 msec to 10 second for the pump to raise the level in the anode separator. In the event of a leak caused by a fault in the either the gas or fluid side of the system, ozone gas may be released into the operatory. The system has the ability to recognize a rapid drop in system pressure causing the production of ozone and delivery of ultrasonic scaling power to be disabled. In addition, the aqueous ozone ultrasonic scaler system 100 may have an internal gaseous ozone gas monitor 112** that will automatically stop aqueous ozone production if the internal (inside the system housing) gaseous ozone levels exceed 100 ppb. Further, in an illustrative embodiment, the fluid pathways of the device are all enclosed except for where ozonated water leaves the insert tip for delivery to the patient's oral cavity.

Figure 16:
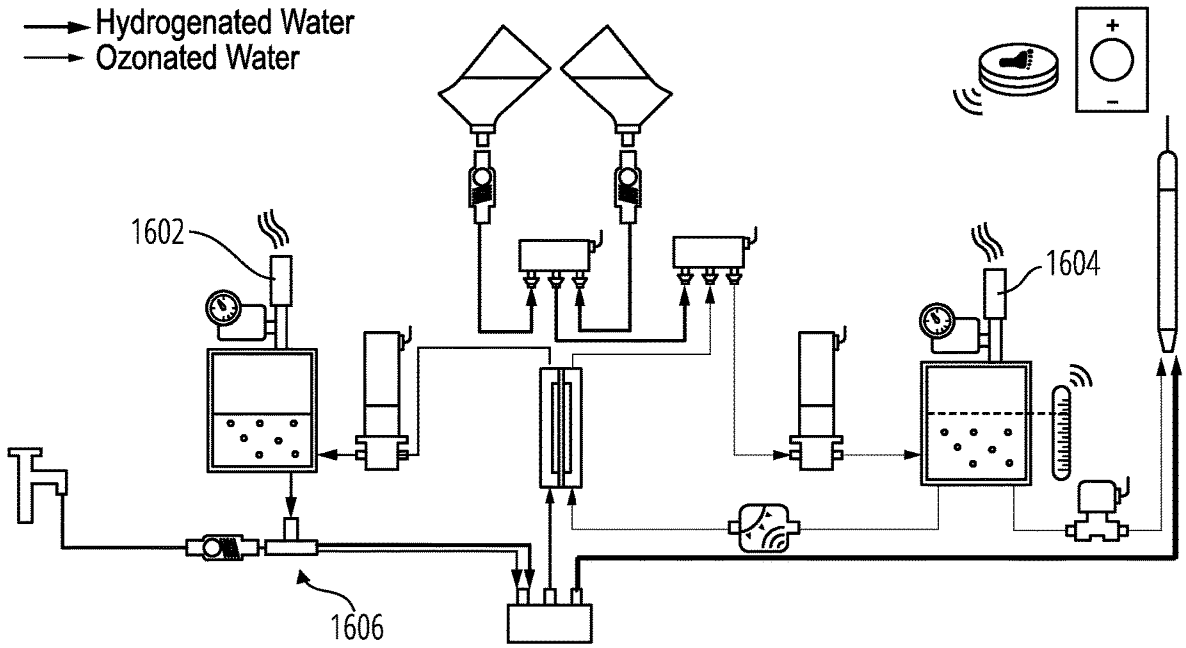
FIG. 16 depicts a system in accordance with one embodiment.

In yet another alternative embodiment, two water packages/water supplies 104 (e.g. spout pouches 704) provide the added convenience of not interrupting a dental procedure if one package empties as shown in FIG. 15. The system will have the ability to sense when a package is empty and automatically switch through the use of the ozone system main control board 406, for example, a sensor may a lack of fluid flow, inability to raise the level in the separator, or simply a loss of fluid. Motor current can also be monitored to identify the presence or absence of fluid in a pump. The use of two pressure relief valves (pressure release valve B 1602 and pressure release valve A 1604) of FIG. 16 ensures that hydrogen and oxygen gas do not mix on the gas side protecting the membrane from cross over gas reactions that might limit its useful life.

Figure 7:
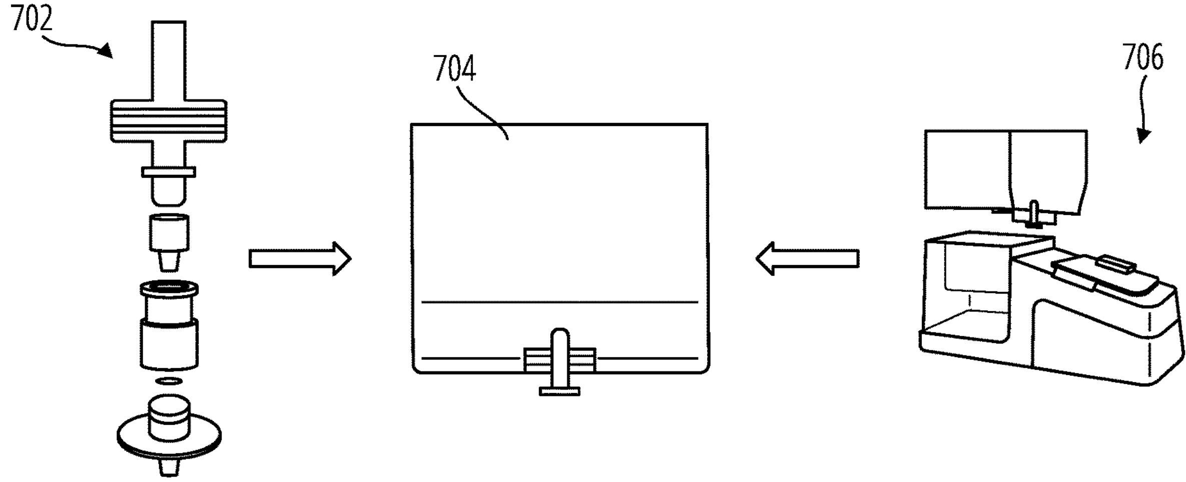
FIG. 7 depicts a sketch of a connection in accordance with one embodiment.
Figure 8:
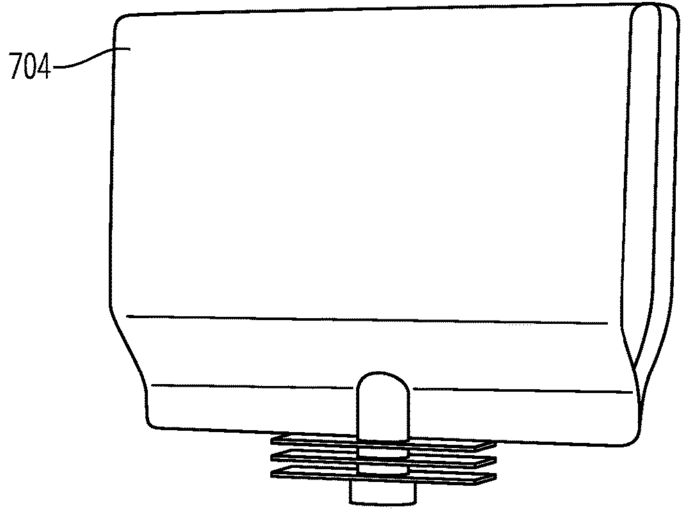
FIG. 8 depicts a sketch of a pouch and connection in accordance with one embodiment.

FIG. 7 depicts a sketch of a connection assembly 702 in accordance with one embodiment. The connection assembly 702 is integrated in a water supply 104 such as a spout pouch 704 (also shown in FIG. 8) for connection to an aqueous ozone ultrasonic scaler 706.

Figure 9:
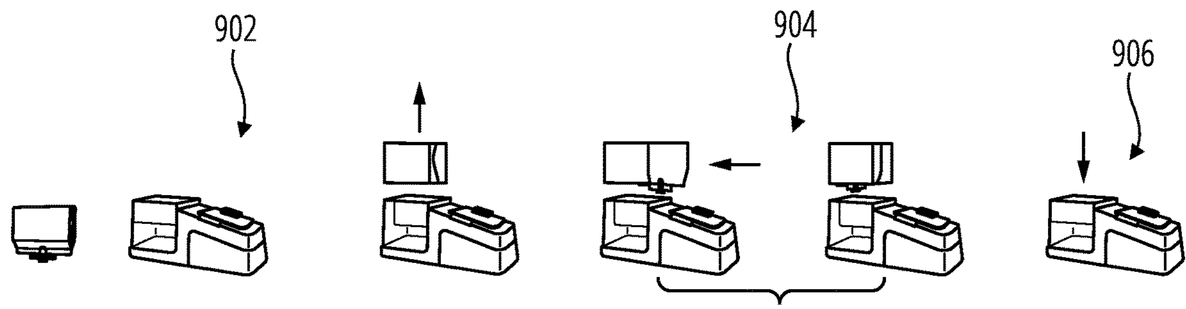
FIG. 9 depicts an interaction accordance with one embodiment.

FIG. 9 depicts an interaction accordance with one embodiment. The interaction comprises a stage 902, wherein an outer lid is removed from the aqueous ozone ultrasonic scaler 706, a stage 904, wherein the spout pouch 704 is inserted into the outer lid and a stage 906 wherein the outer lid is re-inserted into the aqueous ozone ultrasonic scaler 706.

Figure 10:
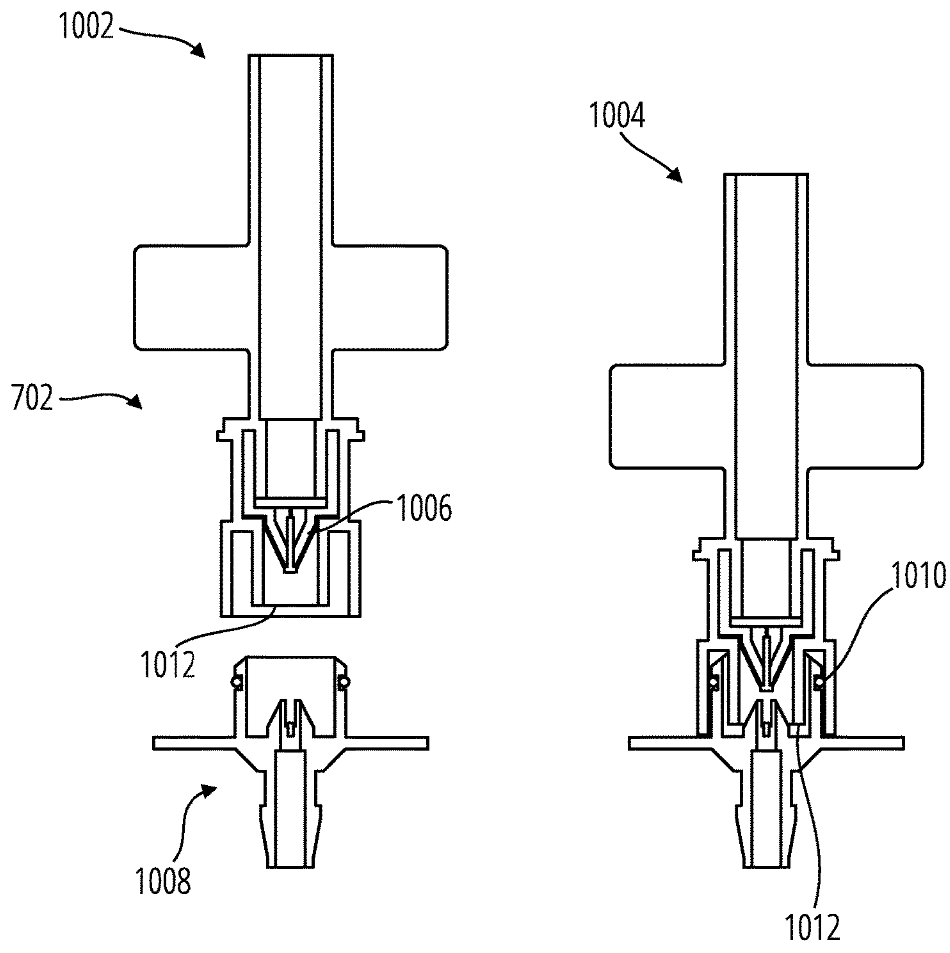
FIG. 10 depicts a sketch of a connection in accordance with one embodiment.

FIG. 10 depicts a sketch of a connection assembly 702 timeline in accordance with one embodiment, with a before connection 1002 and after connection 1004. In an illustrative embodiment, the connection assembly 702, includes, a duck bill 1006 that provides a non-refillable port, a dental instrument connector 1008 for connection to the aqueous ozone ultrasonic scaler 706, an O-ring 1010 that provides a seal from spillage, and a foil seal 1012 that is pierced during insertion as shown in the after connection 1004.

Figure 11:
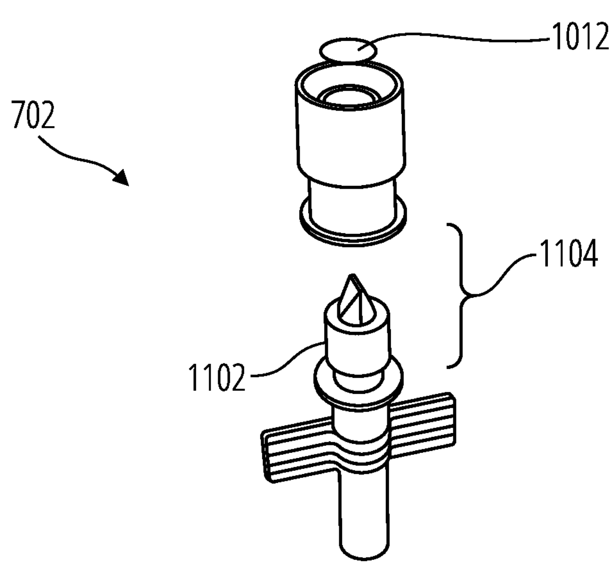
FIG. 11 depicts a sketch of a connection in accordance with one embodiment.

FIG. 11 depicts another view of the connection assembly 702 in accordance with one embodiment which further comprises a duck bill valve 1102 that contained the duck bill 1006. The assembly is connected though an ultrasonic weld/snap/adhesive 1104.

Figure 12:
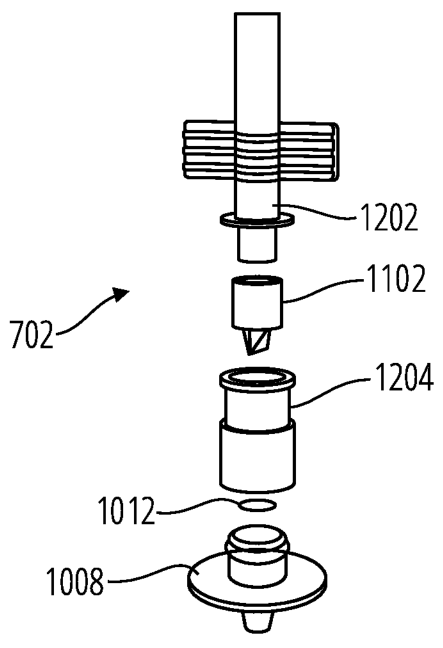
FIG. 12 depicts a sketch of a connection in accordance with one embodiment.

FIG. 12 depicts an exploded view of the connection assembly 702 in more detail. The connection assembly 702 includes a dental instrument connector 1008, a foil seal 1012, a duck bill valve 1102, a spout body 1202, and a spout cap 1204.

Figure 17A:
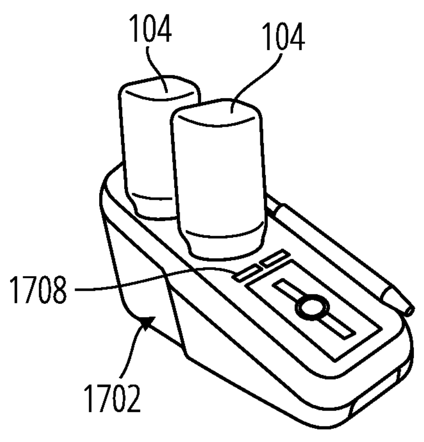
FIG. 17A depicts an alternate configuration of a system in accordance with one embodiment.

FIG. 17A depicts an alternate configuration of the aqueous ozone ultrasonic scaler 706 (aqueous ozone ultrasonic scaler configuration A 1702) in accordance with one embodiment. The aqueous ozone ultrasonic scaler configuration A 1702 comprises two water supplies 104 in a series configuration that causes the aqueous ozone ultrasonic scaler 706 to have a narrow profile. It also comprises level states 1708 that indicate levels of liquid water in water supplies 104.

Figure 17B:
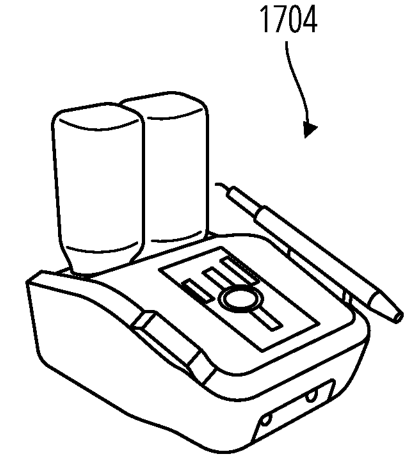
FIG. 17B depicts an alternate configuration of a system in accordance with one embodiment.

FIG. 17B depicts an alternate configuration of the aqueous ozone ultrasonic scaler 706 (aqueous ozone ultrasonic scaler configuration B 1704) in accordance with one embodiment having a two water supplies 104 in a parallel configuration that causes the aqueous ozone ultrasonic scaler 706 to have a broad profile.

Figure 17C:
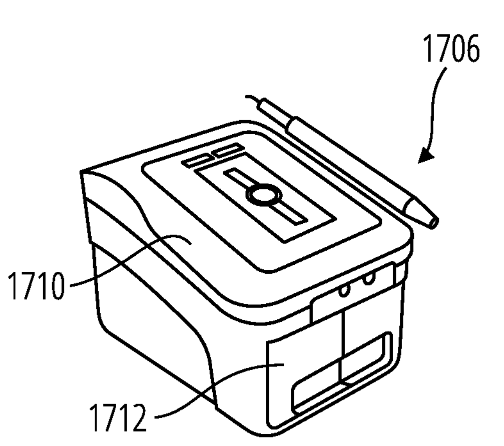
FIG. 17C depicts an alternate configuration of a system in accordance with one embodiment.

FIG. 17C depicts an alternate configuration of the aqueous ozone ultrasonic scaler 706 (aqueous ozone ultrasonic scaler configuration C 1706) in accordance with one embodiment. In this embodiment, the spout pouch 704 are stored in a compartment 1712 underneath user interface 1710.

Figure 17D:
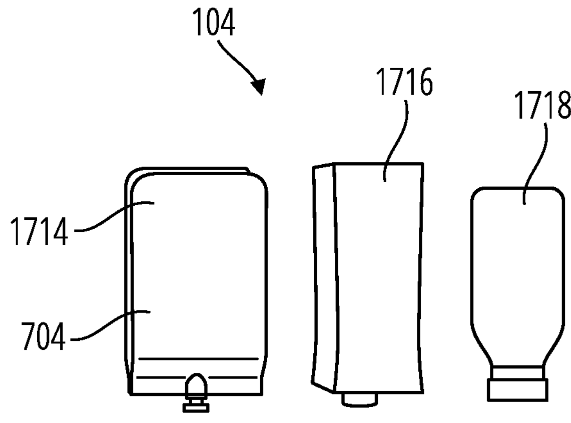
FIG. 17D depicts an alternate configuration of a system in accordance with one embodiment.

FIG. 17D depicts further illustrative shapes of the water supplies 104 including a plastic spout pouch 1714, a carton 1716 and a bottle 1718.

FIG. 18A (aqueous ozone ultrasonic scaler configuration D 1802) and FIG. 18B (aqueous ozone ultrasonic scaler configuration E 1804) depict another alternate configuration of a system in which a plastic spout pouch 1714 and a carton are used in a parallel configuration to produce a scaler with a broad profile, as opposed to a scaler with a narrow profile of FIG. 18C (aqueous ozone ultrasonic scaler configuration F 1806). In any of the configurations discussed herein, the ultrasonic handpiece 108 may be a magnetically coupled handpiece (dual sided) 1808 which is attached to the base of the scaler by magnetic means.

Figure 19A:
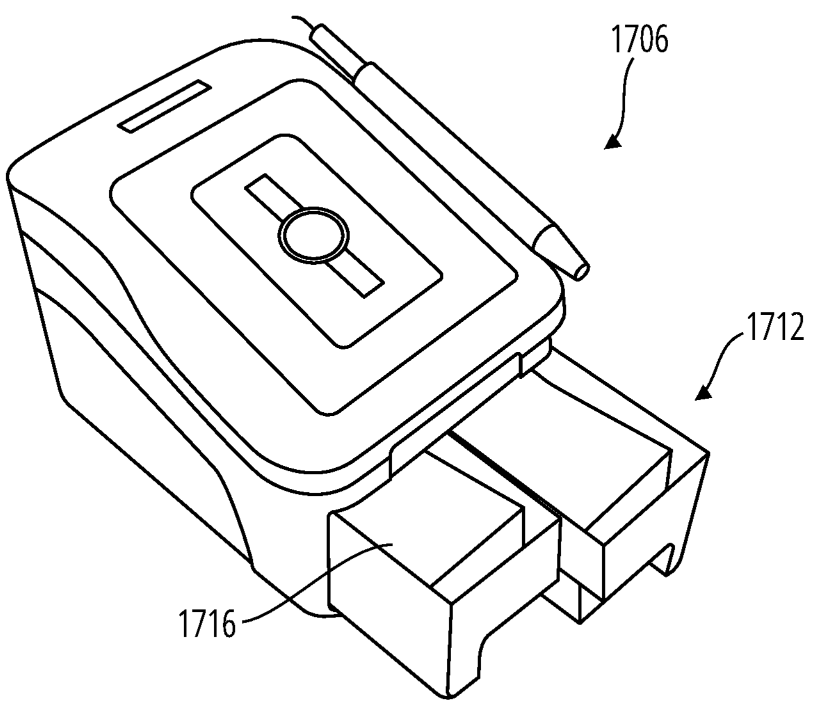
FIG. 19A depicts an alternate configuration of a system in accordance with one embodiment.
Figure 19B:
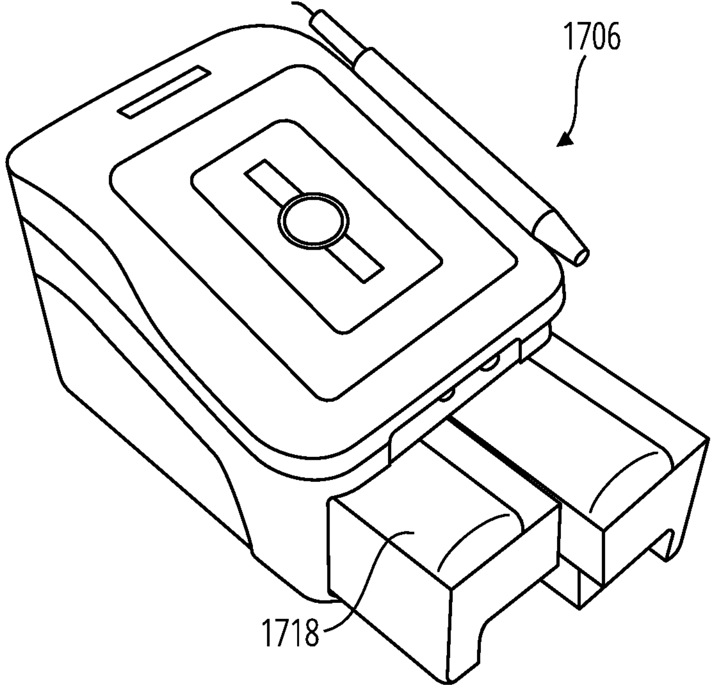

FIG. 19A-FIG. 19B also depict alternate configurations aqueous ozone ultrasonic scaler configuration C 1706 having compartments 1712 that receive the water supply as a carton 1716 or a bottle 1718.

In yet another illustrative embodiment, FIG. 20A depicts a configuration having a base 2002 and a removable interface 2004 and FIG. 20B depicts a handpiece retention port 2006 and a loading tray with illumination 2008 in the compartment 1712 region.

Method

Turning now to FIG. 21, a process 2100 2100 in accordance with an illustrative embodiment will now be described. The process 2100 by delivering deionized water from a water supply 104 as shown in Step 2102. In Step 2104, the water is pumped via a pump such as a primary water pump 118*c* to maintain fluid levels and achieve enough pressure to increase gas solubility and eventually drive the water to a handpiece. In Step 2106, the water is moved through the electrolytic cell such as electrolytic ozone cell 106 in recirculation loops using corresponding pumps (such as air pump 118*a* and air pump 118*b*) of the recirculation loops. Oxygen and ozone gasses are generated on the anode side and hydrogen gas on the cathode side through electrolysis in Step 2108. In the next step, Step 2110, gas that is entrained is dissolved in the water and excess gas is separated from the water being recirculated. The excess gas is vented through the ozone destroyer 114 using a valve 120 such as a pressure release valve. In Step 2112, defined ozone levels are maintained by controlling an amount of current provided to the electrolytic ozone cell 106, such as (~0.5 ppm) to maintain water lines or (4-6 ppm) to deliver clinical efficacy. Step 2114 involves monitoring ozone concentration in the fluid pathway 144 using a uv sensor 110 and controlling the production of ozone by modulating the electrolysis production. A plurality of uv sensors 110 can be used, for example, one for each polarity configuration (polarity switch). In Step 2116, the flow of aqueous ozone from the pressurized system to the ultrasonic handpiece 108 is controlled using a water solenoid valve as the pump(s) maintains defined fluid levels and system pressure. Further, the aqueous ozone ultrasonic scaler system 100 is configured to report a status of for example, water levels, or respond to user request for aqueous ozone water and control safety and efficacy of the system in Step 2118. The process 2100 ends thereafter (Step 2120).

Computer System

Having described the apparatus, reference will now be made to FIG. 22, which shows a block diagram of a computer system 2200 that may be employed in accordance with at least some of the illustrative embodiments herein. Although various embodiments may be described herein in terms of this exemplary computer system 2200, after reading this description, it may become apparent to a person skilled in the relevant art(s) how to implement the disclosure using other computer systems and/or architectures.

In one example embodiment herein, at least some components of the aqueous ozone ultrasonic scaler system 100 such as the ultrasonic control board 404 and the ozone system main control board 406 may form or be included in the computer system 2200 of FIG. 22. The computer system 2200 includes at least one computer processor 2206. The computer processor 2206 may include, for example, a central processing unit (CPU), a multiple processing unit, an application-specific integrated circuit ("ASIC"), a field programmable gate array ("FPGA"), or the like. The computer processor 2206 may be connected to a communication infrastructure 2202 (e.g. a communications bus, a cross-over bar device, a network). In an illustrative embodiment herein, the computer processor 2206 includes a CPU that that controls the electrolytic ozone cell 106 and timing of the ozone formation process.

The display interface 2208 (or other interface such as user interface 402) forwards text, video graphics, and other data from the communication infrastructure 2202 (or from a frame buffer (not shown)) for display on display unit 2214. For example, the display interface 2208 may include a video card with a graphics processing unit or may provide an operator with an interface for controlling the apparatus.

The computer system 2200 may also include an input unit 2210 that may be used, along with the display unit 2214 by an operator of the computer system 2200 to send information to the computer processor 2206. The input unit 2210 may include for example, touchscreen monitor. In one example, the display unit 2214, the input unit 2210, and the computer processor 2206 may collectively form a user interface.

One or more steps providing ozonated water to an ultrasonic scaler handpiece may be stored on a non-transitory storage device in the form of computer-readable program instructions. To execute a procedure, the computer processor 2206 loads the appropriate instructions, as stored on storage device, into memory and then executes the loaded instructions.

The computer system 2200 may further comprise a main memory 2204, which may be a random-access memory ("RAM"), and also may include a secondary memory 2218. The secondary memory 2218 may include, for example, a hard disk drive 2220 and/or a removable-storage drive 2222 (e.g., a floppy disk drive, a magnetic tape drive, an optical disk drive, a flash memory drive, and the like). The removable-storage drive 2222 reads from and/or writes to a removable storage unit 2226 in a well-known manner. The removable storage unit 2226 may be, for example, a floppy disk, a magnetic tape, an optical disk, a flash memory device, and the like, which may be written to and read from by the removable-storage drive 2222. The removable storage unit 2226 may include a non-transitory computer-readable storage medium storing computer-executable software instructions and/or data.

In further illustrative embodiments, the secondary memory 2218 may include other computer-readable media storing computer-executable programs or other instructions to be loaded into the computer system 2200. Such devices may include removable storage unit 2228 and an interface 2224 (e.g., a program cartridge and a cartridge interface); a removable memory chip (e.g., an erasable programmable read-only memory ("EPROM") or a programmable read-only memory ("PROM")) and an associated memory socket; and other removable storage units 2228 and interfaces 2224 that allow software and data to be transferred from the removable storage unit 2228 to other parts of the computer system 2200.

The computer system 2200 may also include a communications interface 2212 that enables software and data to be transferred between the computer system 2200 and external devices. Such an interface may include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCMCIA") interface, Bluetooth®, and the like. Software and data transferred via the communications interface 2212 may be in the form of signals, which may be electronic, electromagnetic, optical or another type of signal that may be capable of being transmitted and/or received by the communications interface 2212. Signals may be provided to the communications interface 2212 via a communications path 2216 (e.g., a channel). The communications path 2216 carries signals and may be implemented using wire or cable, fiber optics, a telephone line, a cellular link, a radiofrequency ("RF") link, or the like. The communications interface 2212 may be used to transfer software or data or other information between the computer system 2200 and a remote server or cloud-based storage (not shown).

One or more computer programs or computer control logic may be stored in the main memory 2204 and/or the secondary memory 2218. The computer programs may also be received via the communications interface 2212. The computer programs include computer-executable instructions which, when executed by the computer processor 2206, cause the computer system 2200 to perform the methods as described hereinafter. Accordingly, the computer programs may control the computer system 2200 and other components of the aqueous ozone ultrasonic scaler system 100.

In another embodiment, the software may be stored in a non-transitory computer-readable storage medium and loaded into the main memory 2204 and/or the secondary memory 2218 using the removable-storage drive 2222, hard disk drive 2220, and/or the communications interface 2212. Control logic (software), when executed by the computer processor 2206, causes the computer system 2200, and more generally the apparatus, to perform the some or all of the methods described herein.

Lastly, in another example embodiment hardware components such as ASICs, FPGAs, and the like, may be used to carry out the functionality described herein. Implementation of such a hardware arrangement so as to perform the functions described herein will be apparent to persons skilled in the relevant art(s) in view of this description.

What is claimed is:

1. A method of providing ozonated water to an ultrasonic scaler handpiece comprising:

delivering water from a water supply to an electrolytic cell of an aqueous ozone ultrasonic scaler system;

delivering current to the electrolytic cell to generate ozone gas in the water delivered to the electrolytic cell;

providing one or more recirculation loops in a fluid pathway to move the water and the generated ozone gas through the electrolytic cell and one or more gas separators that are disposed in a corresponding recirculation loop;

separating gaseous ozone from a flow of the ozonated water that is to be delivered to the ultrasonic scaler handpiece using the one or more gas separators;

measuring with one or more ultraviolet sensors the ozone concentration in the water through an amount of ultraviolet light absorbed by dissolved ozone in the water passing through a water column, wherein the one or more ultraviolet sensors are disposed in the recirculation loop of the fluid pathway, and wherein the aqueous ozone travels from the electrolytic cell into the gas separators and then from the gas separators into the ultraviolet sensor;

controlling, in closed loop with the measurement, a level of the generated ozone gas concentration in the water delivered to the electrolytic cell through an amount of the current delivered to the electrolytic cell in order to generate ozonated water having a defined concentration of dissolved ozone;

wherein a proton-conductive membrane is used in the electrolytic cell and the method further comprises switching an electrical polarity of the electrolytic cell after a defined period of operation time and after verifying that ozone gas in the water has decayed below a threshold level, such that a side of the aqueous ozone ultrasonic scaler system that was a cathode side in a previous operation becomes an anode side in a current operation and another side of the aqueous ozone ultrasonic scaler system that was the anode side in the previous operation becomes the cathode side in the current operation, in order to distribute a membrane degradation, that occurs from an interaction of ozone gas and other oxidative species from the electrolytic cell, over both sides of the electrolytic cell to extend a shelf life of the membrane of the electrolytic cell and eliminate stagnant water and microbial contamination; and delivering the ozonated water to the ultrasonic scaler handpiece.

2. The method of claim 1 further comprising providing one or more pumps to maintain a defined fluid level and pressure of the aqueous ozone ultrasonic scaler system in order to increase solubility of the ozone gas in the water.

3. The method of claim 1, wherein the water delivered from the water supply is deionized water or water obtained from reverse osmosis.

4. The method of claim 1, further comprising:

slowing a flow of the ozonated water entering the one or more gas separators using an inlet baffle such that in order to substantially reduce overturning flow in a chamber of the one or more gas separators and prevent bubbles from being carried to an exit port of the one or more gas separators.

5. An apparatus for providing ozonated water to an ultrasonic scaler handpiece comprising:

an ultrasonic scaler handpiece;

an electrolytic cell having a proton-conductive membrane;

a water supply for delivering water to the electrolytic cell, wherein the electrolytic cell is in connection with the water supply through a fluid pathway and is adapted to receive current to generate ozone gas in the water in order to form ozonated water;

one or more gas separators, wherein each gas separator is disposed in a corresponding recirculation loop of the fluid pathway that also contains the electrolytic cell, said each gas separator is configured to separate gaseous ozone from a flow of ozonated water that is to be delivered to the ultrasonic scaler handpiece;

one or more ultraviolet sensors disposed in said recirculation loop of the fluid pathway, so that the aqueous ozone travels from the electrolytic cell into the gas separators and then from the gas separators into the ultraviolet sensor, and wherein the one or more ultraviolet sensors are adapted to measure dissolved ozone concentration in the water through an amount of ultraviolet light absorbed by dissolved ozone in the water passing through a water column; and a controller configured to switch an electrical polarity of the electrolytic cell after a defined period of operation time and after verifying that ozone gas in the water has decayed below a threshold level, such that a side of the apparatus that was a cathode side in a previous operation becomes an anode side in a current operation and another side of the apparatus that was the anode side in the previous operation becomes the cathode side in the current operation, in order to distribute a membrane degradation, that occurs from an interaction of ozone gas and other oxidative species from the electrolytic cell, over both sides of the electrolytic cell to extend a shelf life of the membrane of the electrolytic cell and eliminate stagnant water and microbial contamination.

6. The apparatus of claim 5, further comprising:

one or more pumps disposed in the fluid pathway to control a pressure of the apparatus in at least a portion of the fluid pathway.

7. The apparatus of claim 5, further comprising:

one or more valves disposed in the fluid pathway to release gas in order to control another pressure of the apparatus in at least a portion of the fluid pathway.

8. The apparatus of claim 5, further comprising:

one or more level sensors connected to the one or more gas separators to measure a level of ozonated water in the gas separators.

9. The apparatus of claim 5, further comprising:

an ozone destroyer disposed in a gas release pathway of one or more gas separators and adapted to convert separated gaseous ozone gas into oxygen.

10. The apparatus of claim 5, wherein the water supply is a spout pouch or a water bottle having a duck bill connection assembly to deliver the water in a single direction.

11. The apparatus of claim 5, wherein the water supply is held in a loading tray in a base of the apparatus.

12. The apparatus of claim 5, wherein a polarity of the electrolytic ozone cell is switchable to reverse a side of the apparatus that produces the ozone gas.

13. The apparatus of claim 5, further comprising:

a light emitting diode (LED) light source and a detector photodiode disposed on opposite ends of each of the one or more ultraviolet sensors, the LED light source configured to project ultraviolet light toward the detector photodiode in order to measure an amount of ultraviolet light absorbed by dissolved ozone, wherein a monitoring photodiode disposed proximate to the LED light source is configured to measure a change in an output intensity of the LED light source in order to compensate for degradation of the LED light source with time.

14. The apparatus of claim 10, wherein the spout pouch or water bottle has a Radio-frequency identification (RFID) label configured to be read to prevent reuse or the use of an alternative water source that does not have said RFID label.

15. A computer system for providing ozonated water to an ultrasonic scaler handpiece comprising a processor configured to perform the steps of:

delivering water from a water supply to an electrolytic cell of an aqueous ozone ultrasonic scaler system;

delivering current to the electrolytic cell to generate ozone gas in the water delivered to the electrolytic cell;

providing one or more recirculation loops in a fluid pathway to move the water and the generated ozone gas through the electrolytic cell and one or more gas separators that are disposed in a corresponding recirculation loop;

separating gaseous ozone from a flow of the ozonated water that is to be delivered to the ultrasonic scaler handpiece using the one or more gas separators;

measuring with one or more ultraviolet sensors the ozone concentration in the water through an amount of ultraviolet light absorbed by dissolved ozone in the water passing through a water column, wherein the one or more ultraviolet sensors are disposed in the recirculation loop of the fluid pathway, and wherein the aqueous ozone travels from the electrolytic cell into the gas separators and then from the gas separators into the ultraviolet sensor;

controlling, in closed loop with the measurement, a level of the generated ozone gas concentration in the water delivered to the electrolytic cell through an amount of the current delivered to the electrolytic cell in order to generate ozonated water having a defined concentration of dissolved ozone;

switching an electrical polarity of the electrolytic cell after a defined period of operation time and after verifying that ozone gas in the water has decayed below a threshold level, such that a side of the aqueous ozone ultrasonic scaler system that was a cathode side in a previous operation becomes an anode side in a current operation and another side of the aqueous ozone ultrasonic scaler system that was the anode side in the previous operation becomes the cathode side in the current operation, in order to distribute a membrane degradation, that occurs from an interaction of ozone gas and other oxidative species from the electrolytic cell, over both sides of the electrolytic cell to extend a shelf life of the membrane of the electrolytic cell and eliminate stagnant water and microbial contamination; and delivering the ozonated water to the ultrasonic scaler handpiece.

16. The computer system of claim 15 wherein the processor is further configured to perform the step of using one or more pumps to maintain a defined fluid level and pressure of the aqueous ozone ultrasonic scaler system in order to increase solubility of the ozone gas in the water.

17. The computer system of claim 15, wherein the water delivered from the water supply is deionized water or water obtained from reverse osmosis.

18. A non-transitory computer-readable storage medium storing a program which, when executed by a computer system, causes the computer system to perform a procedure comprising:

delivering water from a water supply to an electrolytic cell of an aqueous ozone ultrasonic scaler system, wherein a proton-conductive membrane is used in the electrolytic cell;

delivering current to the electrolytic cell to generate ozone gas in the water delivered to the electrolytic cell;

providing one or more recirculation loops in a fluid pathway to move the water and the generated ozone gas through the electrolytic cell and one or more gas separators that are disposed in a corresponding recirculation loop;

separating gaseous ozone from a flow of the ozonated water that is to be delivered to the ultrasonic scaler handpiece using the one or more gas separators;

measuring with one or more ultraviolet sensors the ozone concentration in the water through an amount of ultraviolet light absorbed by dissolved ozone in the water passing through a water column, wherein the one or more ultraviolet sensors are disposed in the recirculation loop of the fluid pathway, and wherein the aqueous ozone travels from the electrolytic cell into the gas separators and then from the gas separators into the ultraviolet sensor;

controlling, in closed loop with the measurement, a level of the generated ozone gas concentration in the water delivered to the electrolytic cell through an amount of the current delivered to the electrolytic cell in order to generate ozonated water having a defined concentration of dissolved ozone;

switching an electrical polarity of the electrolytic cell after a defined period of operation time and after verifying that ozone gas in the water has decayed below a threshold level, such that a side of the aqueous ozone ultrasonic scaler system that was a cathode side in a previous operation becomes an anode side in a current operation and another side of the aqueous ozone ultrasonic scaler system that was the anode side in the previous operation becomes the cathode side in the current operation, in order to distribute a membrane degradation, that occurs from an interaction of ozone gas and other oxidative species from the electrolytic cell, over both sides of the electrolytic cell to extend a shelf life of the membrane of the electrolytic cell and eliminate stagnant water and microbial contamination, and delivering the ozonated water to the ultrasonic scaler handpiece.

* * * * *